United States Patent [19]
Chengappa et al.

[11] Patent Number: 5,981,831
[45] Date of Patent: Nov. 9, 1999

[54] EXO-(1—4)-β-D GALACTANASE

[75] Inventors: Sumant Chengappa, Bedford; Susan A. Hellyer, Cambridge; John S. Reid, Stirling; Jacqueline de Silva, Bedford, all of United Kingdom

[73] Assignee: Unilever Patent Holdings B.V., Netherlands

[21] Appl. No.: 08/696,944

[22] PCT Filed: Feb. 23, 1995

[86] PCT No.: PCT/GB95/00372

§ 371 Date: Aug. 22, 1996

§ 102(e) Date: Aug. 22, 1996

[87] PCT Pub. No.: WO95/23228

PCT Pub. Date: Aug. 31, 1995

[30] Foreign Application Priority Data

Feb. 23, 1994 [GB] United Kingdom ............... 9403423

[51] Int. Cl.$^6$ .............................. A01H 1/04; C07H 21/02
[52] U.S. Cl. ........................................... 800/205; 536/23.6
[58] Field of Search ..................................... 435/410, 411, 435/419, 252.3, 320.1; 536/23.6; 935/14, 22, 23, 30, 35; 800/205

[56] References Cited

FOREIGN PATENT DOCUMENTS

| | | |
|---|---|---|
| 0 341 885 | 11/1989 | European Pat. Off. . |
| 0 479 359 | 4/1992 | European Pat. Off. . |
| WO 92/13945 | 8/1992 | WIPO . |
| WO 95/10622 | 4/1995 | WIPO . |

OTHER PUBLICATIONS

King, G.A., et al., "A Officinalis L. mRNA for beta–galactosidase", EMBL Sequence Database, Feb. 2, 1994, Release 38, Accession No. X77319.

Buckeridge, M.S. et al., "Purification and properties of a novel beta–galactosidase or exo–(1,4)–beta–D–galactanase from the cotyledons of germinated *Lupinus angustifolius L.* seeds", Planta, vol. 192, No. 4, 1994, pp. 502–511.

Raghothama, K.G., et al., "Characterization of an ethylene––regulated flower senescence–related gene from carnation", Plant Molecular Biology, vol. 17, 1991, pp. 61–71.

Edwards, M., et al., "A Beta–D–Galactosidase from Nasturtium (*Tropaeolum majus L.*) Cotyledons", Journal of Biological Chemistry, vol. 263, No. 9, Mar. 25, 1988 US, pp. 4333–4337.

Pressey, R., et al., "Beta–Galactosidease in Ripening Tomatoes", Plant Physiology, vol. 71, 1983, pp. 132–135.

Matheson, N.K., et al., "Alpha–L–Arabinofuranosidases and Beta–D–Galactosidases in Germinating–Lupin Cotyledons", Carbohydrate Research, vol. 57, 1977, pp. 103–116.

Starrett, D.A., et al., "Partial Purification of an Alpha–Galactosidase, Beta–Glactosidase, and Alpha–Mannosidase from Ripening Tomato Fruit", Plant Physiology, vol. 102, No. 1, May 1993, p. 49, (see abstract 261).

*Primary Examiner*—Eggerton A. Campbell
*Attorney, Agent, or Firm*—Cushman Darby & Cushman, IP Group of Pillsbury Madison & Sutro

[57] ABSTRACT

Disclosed is a nucleotide sequence comprising substantially the sequence of nucleotides 229 to 2319 of the sequence shown in FIG. 1 encoding an enzyme having exo-(1→4)-β-D-galactanase activity or a precursor or derivative of such an enzyme, or the functional equivalent of such a sequence. Also disclosed are vectors and hosts comprising the sequence of the invention, and a polypeptide encoded thereby. The nucleotide and amino acid sequences of a functionally equivalent enzyme obtainable from tomato fruit are also disclosed.

13 Claims, 13 Drawing Sheets caacactctt atacaataag agactctcaa aaagtagcaa aataaaaaga cactatatac aaaacagaaa atatttcttc ttctatagaa agacaacatt gcttatatag aaacatagca

```
          M*  F   G   S   R   I   V   M*  E   S   L   M*  S   R
ttttttgtt ATG TTT GGT TCA AGA ATT GTG ATG GAG AGT TTA ATG TCT AGG R   N   F   H   M   V   L   L   L   F   F   W   V   C   Y
AGA AAT TTT CAT ATG GTG TTG CTG TTA TTG TTT TTT TGG GTT TGT TAT V   T   A   S   V   T   Y   D   H   K   A   I   M   I   N   G
GTC ACA GCC TCT GTT ACT TAT GAT CAT AAA GCC ATT ATG ATT AAT GGG Q   R   R   I   L   I   S   G   S   I   H   Y   P   R   S   T
CAG AGA AGA ATT TTG ATC TCT GGT TCC ATT CAC TAT CCA AGA AGC ACA P   Q   M   W   P   D   L   I   Q   K   A   K   D   G   G   L
CCT CAG ATG TGG CCA GAC CTT ATT CAA AAG GCC AAA GAT GGA GGG CTT D   V   I   E   T   Y   V   F   W   N   G   H   E   P   S   P
GAT GTT ATA GAG ACT TAT GTG TTC TGG AAT GGA CAT GAA CCT TCT CCT G   K   Y   Y   F   E   D   R   F   D   L   V   G   F   I   K
GGA AAA TAT TAT TTT GAG GAT AGG TTT GAC CTT GTT GGG TTC ATA AAG L   V   Q   Q   A   G   L   F   V   H   L   R   I   G   P   F
TTG GTT CAG CAA GCT GGT CTA TTT GTT CAT CTC AGG ATT GGT CCT TTC I   C   A   E   W   N   F   G   G   F   P   V   W   L   K   Y
ATA TGT GCT GAA TGG AAC TTT GGA GGA TTT CCT GTT TGG CTC AAA TAT V   P   G   I   A   F   R   T   D   N   E   P   F   K   E   A
GTT CCT GGT ATT GCT TTC AGA ACA GAC AAT GAG CCT TTC AAG GAG GCA M   Q   K   F   T   E   K   I   V   N   I   M   K   A   E   K
ATG CAA AAA TTC ACT GAG AAG ATT GTA AAT ATA ATG AAA GCA GAG AAG L   F   Q   S   Q   G   G   P   I   I   L   S   Q   I   E   N
TTG TTT CAA TCC CAG GGA GGT CCA ATA ATT CTG TCT CAG ATA GAG AAT E   Y   G   P   V   E   W   E   I   G   A   P   G   K   A   Y
GAG TAT GGA CCA GTG GAA TGG GAA ATT GGT GCT CCT GGA AAA GCT TAT T   K   W   A   A   Q   M   A   V   G   L   D   T   G   V   P
ACC AAA TGG GCT GCT CAA ATG GCT GTA GGT CTA GAT ACT GGT GTC CCA W   V   M   C   K   Q   E   D   A   P   D   P   I   I   D   T
TGG GTT ATG TGC AAG CAA GAA GAT GCA CCT GAT CCT ATT ATT GAT ACC C   N   G   F   Y   C   E   N   F   T   P   N   K   N   Y   K
TGC AAT GGA TTT TAC TGT GAA AAC TTC ACT CCA AAC AAG AAC TAC AAA P   K   L   W   T   E   N   W   T   G   W   Y   T   A   F   G
CCC AAA TTG TGG ACA GAA AAT TGG ACT GGC TGG TAC ACT GCT TTT GGT
```

Fig. 1A

```
G   A   T   P   Y   R   P   A   E   D   I   A   F   S   V   A
GGT GCA ACC CCT TAT AGA CCA GCA GAA GAT ATA GCA TTT TCA GTT GCC

R   F   I   Q   N   R   G   S   L   F   N   Y   Y   M   Y   H
AGA TTC ATT CAG AAT CGC GGC TCA CTC TTT AAC TAC TAT ATG TAT CAT

G   G   T   N   F   G   R   T   S   N   G   L   F   V   A   T
GGA GGA ACT AAC TTT GGC CGG ACA TCG AAT GGC CTC TTC GTT GCC ACA

S   Y   D   Y   D   A   P   I   D   E   Y   G   L   L   N   E
AGT TAT GAC TAT GAT GCT CCC ATT GAT GAA TAT GGA CTT CTA AAT GAA

P   K   W   G   H   L   R   E   L   H   R   A   I   K   Q   C
CCA AAA TGG GGG CAT CTG AGA GAA TTA CAT AGA GCA ATA AAA CAA TGC

E   S   A   L   V   S   V   D   P   T   V   S   W   P   G   K
GAG TCG GCT TTA GTG TCG GTG GAT CCC ACA GTG TCA TGG CCT GGA AAA

N   L   E   V   H   L   Y   K   T   E   S   A   C   A   A   F
AAC CTT GAG GTA CAT TTG TAC AAG ACA GAG TCT GCC TGT GCT GCA TTT

L   A   N   Y   N   T   D   Y   S   T   Q   V   K   F   G   N
CTT GCA AAT TAT AAC ACC GAC TAT TCA ACG CAA GTT AAA TTC GGA AAT

G   Q   Y   D   L   P   P   W   S   I   S   I   L   P   D   C
GGA CAA TAT GAT CTA CCA CCT TGG TCT ATC AGT ATT CTT CCT GAC TGC

K   T   E   V   F   N   T   A   K   V   N   S   P   R   L   H
AAA ACT GAA GTT TTC AAC ACT GCA AAG GTT AAT TCC CCG AGA TTA CAT

R   K   M   T   P   V   N   S   A   F   A   W   Q   S   Y   N
AGG AAA ATG ACT CCA GTA AAC AGT GCA TTT GCT TGG CAG TCA TAC AAT

E   E   P   A   S   S   S   E   N   D   P   V   T   G   Y   A
GAA GAA CCT GCA TCA TCA AGC GAA AAT GAT CCC GTC ACA GGA TAT GCA

L   W   E   Q   V   G   V   T   R   D   S   S   D   Y   L   W
CTA TGG GAG CAG GTT GGC GTG ACC CGC GAT TCT TCC GAT TAT TTG TGG

Y   L   T   D   V   N   I   G   P   N   D   I   K   D   G   K
TAC CTG ACA GAT GTC AAC ATT GGT CCT AAT GAT ATA AAG GAT GGG AAA

W   P   V   L   T   A   M   S   A   G   H   V   L   N   V   F
TGG CCT GTT CTG ACA GCA ATG TCA GCA GGT CAT GTT CTG AAT GTT TTC

I   N   G   Q   Y   A   G   T   A   Y   G   S   L   D   D   P
ATC AAT GGT CAA TAT GCA GGA ACT GCA TAT GGG AGT CTA GAT GAT CCT

R   L   T   F   S   Q   S   V   N   L   R   V   G   N   N   K
AGA TTA ACA TTT AGT CAA AGT GTG AAT CTG AGA GTT GGC AAT AAC AAG
```

Fig. 1B

```
I   S   L   L   S   V   S   V   G   L   A   N   V   G   T   H
ATT TCT TTA CTT AGT GTT TCC GTT GGT CTC GCG AAT GTT GGT ACT CAC

F   E   T   W   N   T   G   V   L   G   P   V   T   L   T   G
TTT GAG ACA TGG AAT ACT GGA GTG CTT GGT CCA GTC ACA CTG ACA GGT

L   S   S   G   T   W   D   L   S   K   Q   K   W   S   Y   K
CTA AGT AGC GGA ACA TGG GAT CTT TCG AAG CAA AAA TGG TCT TAC AAG

I   G   L   K   G   E   S   L   S   L   H   T   E   A   G   S
ATT GGT CTG AAA GGT GAA AGC TTG AGC CTT CAT ACT GAA GCT GGG AGT

N   S   V   E   W   V   Q   G   S   L   V   A   K   K   Q   P
AAC TCT GTT GAA TGG GTA CAA GGA TCT TTA GTG GCT AAA AAA CAA CCT

L   A   W   Y   K   T   T   F   S   A   P   A   G   N   D   P
TTG GCA TGG TAT AAG ACA ACT TTT AGC GCA CCA GCC GGC AAC GAT CCG

L   A   L   D   L   G   S   M   G   K   G   E   V   W   V   N
TTG GCT CTG GAT TTA GGT AGC ATG GGT AAG GGT GAA GTA TGG GTA AAT

G   Q   S   I   G   R   H   W   P   G   N   K   A   R   G   N
GGT CAA AGC ATT GGA CGC CAT TGG CCT GGA AAT AAA GCT CGT GGT AAT

C   G   N   C   N   Y   A   G   T   Y   T   D   T   K   C   L
TGC GGC AAT TGT AAT TAC GCT GGA ACT TAT ACC GAT ACA AAA TGC TTA

A   N   C   G   Q   P   S   Q   R   W   Y   H   V   P   R   S
GCA AAC TGT GGA CAA CCC TCC CAA AGA TGG TAT CAT GTT CCT CGG TCA

W   L   R   S   G   G   N   Y   L   V   V   L   E   E   W   G
TGG CTG AGA TCG GGT GGT AAC TAC TTG GTT GTG CTA GAA GAA TGG GGA

G   D   P   N   G   I   A   L   V   E   R   T   Stop
GGT GAT CCT AAT GGA ATT GCT TTG GTG GAA AGA ACA TAA    agtgtatt
```
catgtgatac caaatgtaca tgttatgtac atagtgaaac tattatgctg aatattgttc
catatactac attacagggt ttgtgtcaca atgaacattg agtccttaaa cattggtata
gaagggaaag agttgaatac ccaaaatggg tcaaaatact acattgtcct agaaatagat
ttctttcatt ttctatatca actattatgt aagaacaaat tgaaagtaat actaataaat
agtgatgcat ttggattaaa aaaaaaaaaa aaaaaaaaaa aaaaaaaaaa aaaaaaa

Fig. 1C

```
60 kDa      S  V  T  Y  D  H  K  A  I  M  I  N  G  Q  R  R  I
            L  I  S 45 kDa      S  V  T  Y  D  H  K  A  I  M  I  N 15 kDa      V  A  K  K  Q  P  L  A  W  Y  -  T  T  -  -  A
```

```
            A           T        A     A     A
5' AT  CAT  GAT  IGC  CTT  GTG  GTC  GTA 3'
            T
```

```
1   M L C G K E N N V M K M M L V - - Y V F V L I T L - - I    CARSR12.pro
1   M F - - G S R I V M E S L M S R R N F H M V L L L F F W V  LEG11CON.pro 25  S C V Y G N V W Y D Y R A I K I N D Q R R I L L S G S I H Y  CARSR12.pro
29  C Y V T A S V T Y D H K A I M I N G Q R R I L I S G S I H Y  LEG11CON.pro 55  P R S T P E M W P D I I E K A K D S Q L D V I Q T Y V F W N  CARSR12.pro
59  P R S T P Q M W P D L I Q K A K D G G L D V I E T Y V F W N  LEG11CON.pro 85  G H E P S E G K Y Y F E G R Y D L V K F I K L I H Q A G L F  CARSR12.pro
89  G H E P S P G K Y Y F E D R F D L V G F I K L V Q Q A G L F  LEG11CON.pro 115 V H L R I G P F F A C A E W N F G G F P P V W L K Y V P G I E F  CARSR12.pro
119 V H L R I G P F F I C A E W N F G G F P P V W L K Y V P G I A F  LEG11CON.pro 145 R T D N G P F K E K M Q V F T T K I V D M M K A E K L F H W  CARSR12.pro
149 R T D N E P F K E A M Q K F T E K I V N I M K A E K L F Q S  LEG11CON.pro 175 Q G G P I I L N Q I E N E Y G P V E W E I G A P G K A Y T H  CARSR12.pro
179 Q G G P I I L S Q I E N E Y G P V E W E I G A P G K A Y T K  LEG11CON.pro 205 W A A Q M A Q S L N A G V P W I M C K Q D S D V P D N V I D  CARSR12.pro
209 W A A Q M A V G L D T G V P W V M C K Q E - D A P D P I I D  LEG11CON.pro 235 T C N G F Y C E G F V P K D K S K P K M W T E N W T G W Y T  CARSR12.pro
238 T C N G F Y C E N F T P N K N Y K P K L W T E N W T G W Y T  LEG11CON.pro
```

```
265  E Y G K P V P Y R P A E D V A F S V A R F I Q N G G S F M N   CARSR12.pro
268  A F G G A T P Y R P A E D I A F S V A R F I Q N R G S L F N   LEG11CON.pro 295  Y Y M F H G G T N F E - T T A G R F V S T S Y D Y D A P L D   CARSR12.pro
298  Y Y M Y H G G T N F G R T S N G L F V A T S Y D Y D A P I D   LEG11CON.pro 324  E Y G L P R E P K Y T H L K N L H K A I K M C E P A L V S S   CARSR12.pro
328  E Y G L L N E P K W G H L R E L H R A I K Q C E S A L V S V   LEG11CON.pro 354  D A K V T N L G S N Q E A H V Y S S N S G - C A A F L A N Y   CARSR12.pro
358  D P T V S W P G K N L E V H L Y K T E S - A C A A F L A N Y   LEG11CON.pro 384  D P K W S V K V T F S G M E F E L P A W S I S I L P D C K K   CARSR12.pro
387  N T D Y S T Q V K F G N G Q Y D L P P W S I L P D C K T       LEG11CON.pro 414  E V Y N T A R V N E P S P K L H S K M T P V I S N L N W Q S   CARSR12.pro
417  E V F N T A K V - - N S P R L H R K M T P V N S A F A W Q S   LEG11CON.pro 444  Y S D E V P T A D S P G T F R E K K L Y E Q I N M T W D K S   CARSR12.pro
445  Y N E E P A S S S E N D P V T G Y A L W E Q V G V T R D S S   LEG11CON.pro 474  D Y L W Y M T D V V L D G N E G F L K K G D E P W L T V N S   CARSR12.pro
475  D Y L W Y L T D V N I G P N D - - I K D G K W P V L T A M S   LEG11CON.pro 504  A G H V L H V F V N G Q L Q G H A Y G S L A K P Q L T F S Q   CARSR12.pro
503  A G H V L N V F I N G Q Y A G T A Y G S L D D P R L T F S Q   LEG11CON.pro
```

Fig. 4B

| | | | | | | |
|---|---|---|---|---|---|---|
| 534 | K V K M T A G V N R I | S L L S A V V G L A N V G W H F E R Y | CARSR12.pro |
| 533 | S V N L R V G N N K I | S L L S V S V G L A N V G T H F E T W | LEG11CON.pro |
| 564 | N Q ⌐G V L G P V T L¬ | S G L N E G T R D L T W Q Y W S Y K I G | CARSR12.pro |
| 563 | N T ⌊G V L G P V T L⌋ | S S G T W D L S K Q K W S Y K I G | LEG11CON.pro |
| 594 | T K G E E Q Q V Y N | S G G S S H V Q W G P P A W - - K Q P | CARSR12.pro |
| 593 | L K G E S L H T E A | G S N S V E W V Q G S L V A K K Q P | LEG11CON.pro |
| 621 | L V W Y K T T F D A P G | ⌐G N D P L A L D L G S¬ M G K G Q A W | CARSR12.pro |
| 623 | L A W Y K T T F S A P A | ⌊G N D P L A L D L G S⌋ M G K G E V W | LEG11CON.pro |
| 651 | I N G Q S I G R H W S N N I A K G S | ⌐C N D N C N Y A G T Y T¬ | CARSR12.pro |
| 653 | V N G Q S I G R H W P G N K A R G | ⌊N C G - N C N Y A G T Y T⌋ | LEG11CON.pro |
| 681 | E T K C L S D C G K S S Q K W Y H V P R S W L Q P R G N L L | | CARSR12.pro |
| 682 | D T K C L A N C G Q P S Q R W Y H V P R S W L R S G G N Y L | | LEG11CON.pro |
| 711 | V V F E E W G G D T K W V S L V K R T I A | | CARSR12.pro |
| 712 | V V L E E W G G D P N G I A L V E R T - | | LEG11CON.pro |

Fig. 4C

```
TTAAAAAGGCACAATCTTGATAGAAAAGGAGATAAATTTTACATGGTTGTACGCTTATACTAATGTTGAATGTGTTGGTGTTGTTGG    90
                                  M  G  C  T  L  I  L  M  L  N  V  L  L  V  L  L
GTTCATGGGTTTTTTCTGGAACAGCTTCTGTTTCATATGACCATAGGGCTATTATTGTAAATGGACAAAGAAGAATACTTATTTCTGGTT  180
 G  S  W  V  F  S  G  T  A  S  V  S  Y  D  H  R  A  I  I  V  N  G  Q  R  R  I  L  I  S  G
CTGTTCATTATCCAAGAAGCACTCCTGAGATGTGGCCAGGTATTATTCAAAAGGCTAAAGAAGGAGGTGTGGATGTGATTCAGACTTATG  270
 S  V  H  Y  P  R  S  T  P  E  M  W  P  G  I  I  Q  K  A  K  E  G  G  V  D  V  I  Q  T  Y
TTTTCTGGAATGGACATGAGCCTCAACAAGGGAAATATTATTTTGAAGGGAGATATGATTTAGTGAAGTTTATTAAGCTGGTGCACCAAG  360
 V  F  W  N  G  H  E  P  Q  Q  G  K  Y  Y  F  E  G  R  Y  D  L  V  K  F  I  K  L  V  H  Q
CAGGACTTTATGTCCATCTTAGAGTTGGACCTTTGGACCTTTCCTGTTTGGCTGAAATATGTTCCAG  450
 A  G  L  Y  V  H  L  R  V  G  P  Y  A  C  A  E  W  N  F  G  G  F  P  V  W  L  K  Y  V  P
GTATCAGTTTCAGAACAGATAATGGACCTTTCAAGGCTGCAATGCAAATGCAAAAATTTACTGCCAAGATTGTCAATATGATGAAAGCGGAACGTT  540
 G  I  S  F  R  T  D  N  G  P  F  K  A  A  M  Q  K  F  T  A  K  I  V  N  M  M  K  A  E  R
TGTATGAAACTCAAGGGGGCCAATAATTTTATCTCAGATTGAGAATGAATGGACCCATGGAATGGGAGCACCAGGTAAAT  630
 L  Y  E  T  Q  G  G  P  I  I  L  S  Q  I  E  N  E  Y  G  P  M  E  W  E  L  G  A  P  G  K
CTTACGCACAGTGGGCCGCCAAAATGGCTGTGGGTCTTGACACTGGTGTCCCATGGGTTATGTGCAAGCAAGACGATGCCCCTGATCCTA  720
 S  Y  A  Q  W  A  A  K  M  A  V  G  L  D  T  G  V  P  W  V  M  C  K  Q  D  D  A  P  D  P
TTATAAATGCTTGCAATGGCTTCTACTGTGACTACTTTTCTCCAAACAAGGCTTATAAACCAAAGATATGGACTGAAGCTGGACTGCAT  810
 I  I  N  A  C  N  G  F  Y  C  D  Y  F  S  P  N  K  A  Y  K  P  K  I  W  T  E  A  W  T  A
GGTTTACTGGTTTTGGAAATCCAGTTCCTTACCGTCCTGCTGAGGACTTGGCATTTTCTGTTGCAAAATTTATCAGAAGGAGGTTCCT  900
 W  F  T  G  F  G  N  P  V  P  Y  R  P  A  E  D  L  A  F  S  V  A  K  F  I  Q  K  G  G  S
TCATCAATTATTACATGTATCATGGAGGAACAAACTTTGGACGACTGCTGGTCCATTATTGCTACTAGTGACTATGATGCAC  990
 F  I  N  Y  Y  M  Y  H  G  G  T  N  F  G  R  T  A  G  G  P  F  I  A  T  S  Y  D  Y  D  A
```

Fig. 5A

```
CACTTGATGATGAATATGGATTATTGCGACAACCAAATGGGGTCACCTGAAAGATCTGCATAGAGCAATAAAGCTTTGTGAACCAGCTTTAG 1080
 P  L  D  E  Y  G  L  L  R  Q  P  K  W  G  H  L  K  D  L  H  R  A  I  K  L  C  E  P  A  L

TCTCTGGAGATCCAGCTGTGACAGCACTTGGACACCAGCAGGAGGCCCATGTTTTTAGGTCGAAGGCTGGCTCTTGTGCTGCATTCCTTG 1170
 V  S  G  D  P  A  V  T  A  L  G  H  Q  Q  E  A  H  V  F  R  S  K  A  G  S  C  A  A  F  L

CTAACTACGACCAACACTCTTTTGCTACTGTGTCATTTGCAAACAGGCATTACAACTTGCCACCATGGTCAATCAGCATTCTTCCCGACT 1260
 A  N  Y  Q  Q  H  S  F  A  T  V  S  F  A  N  R  H  Y  N  L  P  P  W  S  I  S  I  L  P  D

GCAAGAACACTGTATTTAATACAGCACGGATCGGTGCTCAAAGTGCTCAGATGAAGATGACTCCAGTCAGCAGAGGATTGCCCTGGCAGT 1350
 C  K  N  T  V  F  N  T  A  R  I  G  A  Q  S  A  Q  M  K  M  T  P  V  S  R  G  L  P  W  Q

CATTCAATGAAGAGACATCATCTTATGAAGACAGTAGTTTTACAGTTGTTGGGCTATTGGAACAGATAAATACAACAAGAGACGTGTCTG 1440
 S  F  N  E  E  T  S  S  Y  E  D  S  S  F  T  V  V  G  L  L  E  Q  I  N  T  T  R  D  V  S

ATTAYTTGTGGTATTCAACAGATGTCAAGATTGATTCAAGAGAAAAGTTTTTGAGAGGCGGAAAATGCCTTGGCTTACGATCATGTCAG 1530
 D  Y  L  W  Y  S  T  D  V  K  I  D  S  R  E  K  F  L  R  G  G  K  W  P  W  L  T  I  M  S

CTGGGCATGCATTGCATGTTTTTGTGAATGGTCAATTAGCAGGAACTGCATATGGAAGTTTAGAAAAACCGAAACTAACTTTCAGTAAAG 1620
 A  G  H  A  L  H  V  F  V  N  G  Q  L  A  G  T  A  Y  G  S  L  E  K  P  K  L  T  F  S  K

CCGTAAATCTGAGAGCAGGAGTGTTAACAAGATTTCTCACTGAGGACATTGCTGTTGGCCTTCCGAATATCGGCCCACATTTTGAGACATGGA 1710
 A  V  N  L  R  A  G  V  N  K  I  S  L  L  S  I  A  V  G  L  P  N  I  G  P  H  F  E  T  W

ATGCTGGTGTTCTTGGGCCAGTCTCATTCACTGGTCTTGACGAGGGAAAAGAGATTTAACATGGCAGAAATGGTTCTACAAGGTTGGTC 1800
 N  A  G  V  L  G  P  V  S  L  T  G  L  D  E  G  K  R  D  L  T  W  Q  K  W  F  Y  K  V  G

TAAAAGGAGAAGCCCTGAGTCTTCATTCACTCAGTGGTAGCCCATCCGTGGAGTGGGTGGAAGGTCTTTAGTGGCACAGAAGCAGCCAC 1890
 L  K  G  E  A  L  S  L  H  S  L  S  G  S  P  S  V  E  W  V  E  G  S  L  V  A  Q  K  Q  P

TCAGTTGGTATAAGACTACATTCAATGCTCCAGATGGAAATGAACCTTTGGCTTTAGATATGAATACCATGGCAAAGGTCAAGTATGGA 1980
 L  S  W  Y  K  T  T  F  N  A  P  D  G  N  E  P  L  A  L  D  M  N  T  M  G  K  G  Q  V  W
```

Fig. 5B

```
TAAATGGTCAGAGCCTCGGACGCCACTGGCCTGCATATAAATCATCTGGAAGTTGTAGTGTCTGTAACTATACTGGCTGGTTTGATGAGA 2070
 I  N  G  Q  S  L  G  R  H  W  P  A  Y  K  S  S  G  S  C  S  V  C  N  Y  T  G  W  F  D  E

AAAAGTGCCTAACTAACTGTGGTGAGGGCTCACACAAGATGGTACCCACGTACCCCGTCTTGGCTGTATCCTACTGGAAATTTGTTAGTTG 2160
 K  K  C  L  T  N  C  G  E  G  S  Q  R  W  Y  H  V  P  R  S  W  L  Y  P  T  G  N  L  L  V

TATTCGAGGAATGGGAGGAGAGATCCTTATGGAATCACTTTAGTCAAAAGAGAAATAGGGAGTGTTTGTGCTGATATATATGAGTGGCAAC 2250
 V  F  E  E  W  G  G  D  P  Y  G  I  T  L  V  K  R  E  I  G  S  V  C  A  D  I  Y  E  W  Q

CACAGTTATTGAATTGGCAGAGGCTAGTATCTGGTAAGTTTGACAGACCTCTCAGACCTTAAGTGTGCACCTGGTCAGA 2340
 V  F  E  E  W  G  G  D  P  Y  G  I  T  L  V  K  R  E  I  G  S  V  C  A  D  I  Y  E  W  Q

CACAGTTATTGAATTGGCAGAGGCTAGTATCTGGTAAGTTTGACAGACCTCTCAGACCTTAAGTGTGCACCTGGTCAGA 2340
 P  Q  L  N  W  Q  R  L  V  S  G  K  F  D  R  P  L  R  P  K  A  H  L  K  C  A  P  G  Q

AGATTTCTTCAATCAAATTTGCAAGCTTTGGAACACCAGAGGGAGTTGTGGGAACTTCCAGCAGGAAGCTGCCATGCTCCCGGCTCAT 2430
 R  F  L  Q  S  N  L  Q  A  L  E  H  Q  R  E  L  W  E  L  P  A  G  S  C  H  P  A  L  H

ATGATGCTTTCAAAAGAATTGTGTTGGGAAAAGAGTCTTGCTCAGTACAGTAACACCAGAGAATTTGGAGGTGATCCATGTCGAAACG 2520
 K  I  S  S  I  K  F  A  S  F  G  T  P  E  G  V  C  G  N  F  Q  Q  G  S  C  H  A  P  R  S

ATGATGCTTTCAAAAGAATTGTGTTGGGAAAAGAGTCTTGCTCAGTACAGTAACACCAGAGAATTTGGAGGTGATCCATGTCGAAACG 2520
 Y  D  A  F  K  K  N  C  V  G  K  E  S  C  S  V  Q  V  T  P  E  N  F  G  G  D  P  C  R  N

TTCTAAAGAAACTCTCAGTGGAAGCCATTTGTAGTTGATAATTCTGAGTATACAAGTGAAAAATACTTGAACCACTCATATAAACATTT 2610
 V  L  K  K  L  S  V  E  A  I  C  S

TTCAACGAGCTACTAGACATCCATTAACCACACTACCATTTTTTGGCTTTGCTGGGGTTGAAGTTGTACAGTTAAGCAACACACCTCT 2700

TTGATCAAAGCTCACCTGATTATGAAGATGATTGACGAAAGATTCTGTACATGTAAGGTTTCGTCTAATTACACATACAGATATGATTCT 2790

TGATGAATCGATGTGCAAATTTTGTTTGTGTTAGGGTGAGAGAGACTTGAAAAGCATTTTGCTTTCATGATGTTCTACATTATACAATCA 2880

TAATGTAAGTAAGCAAGCAATAATTCATTGCTTTGCACATTGAAAAAAAAAAAAAAAAAAA 2944
```

Fig. 5C

```
  1   M F G S R I V M E S L M S R R N F H M V L L L L F F W V C Y     LEG11CON.pro
  1   M G C T L I L M - - - - - - - - - - - - L N V L L V L L G S W V F S     CONTIG.TEG1.PRO 31   V T A S V T Y D H K A I M I N G Q R R I L I S G S I H Y P R     LEG11CON.pro
 23   G T A S V S Y D H R A I I V N G Q R R I L I S G S V H Y P R     CONTIG.TEG1.PRO 61   S T P Q M W P D L I Q K A K D G G L D V I E T Y V F W N G H     LEG11CON.pro
 53   S T P E M W P G I I Q K A K E G G V D I Q T Y V F W N G H     CONTIG.TEG1.PRO 91   E P S P G K Y Y F E D R F D L V G F I K L V Q Q A G L F V H     LEG11CON.pro
 83   E P Q Q G K Y Y F E G R Y D L V K F I K L V H Q A G L Y V H     CONTIG.TEG1.PRO 121   L R I G P F I C A E W N F G G F P P V W L K Y V P G I A F R T     LEG11CON.pro
113   L R V G P Y A C A E W N F G G F P P V W L K Y V P G I S F R T     CONTIG.TEG1.PRO 151   D N E P F K E A M Q K F T E K I V N I M K A E K L F Q S Q G     LEG11CON.pro
143   D N G P F K A A M Q K F T A K I V N M M K A E R L Y E T Q G     CONTIG.TEG1.PRO 181   G P I I L S Q I E N E Y G P V E W E I G A P G K A Y T K W A     LEG11CON.pro
173   G P I I L S Q I E N E Y G P M E W E L G A P G K S Y A Q W A     CONTIG.TEG1.PRO 211   A Q M A V G L D T G V P W V M C K Q E D A P D P I I D T C N     LEG11CON.pro
203   A K M A V G L D T G V P W V M C K Q D D A P D P I I N A C N     CONTIG.TEG1.PRO 241   G F Y C E N F T P N K N Y K P K L W T E N W T G W Y T A F G     LEG11CON.pro
233   G F Y C D Y F S P N K A Y K P K I W T E A W T A W F T G F G     CONTIG.TEG1.PRO 271   G A T P Y R P A E D I A F S V A R F I Q N R G S L F N Y Y M     LEG11CON.pro
263   N P V P Y R P A E D L A F S V A K F I Q K G G S F I N Y Y M     CONTIG.TEG1.PRO 301   Y H G G T N F G R T S N G L F V A T S Y D Y D A P I D E Y G     LEG11CON.pro
293   Y H G G T N F G R T A G G P F I A T S Y D Y D A P L D E Y G     CONTIG.TEG1.PRO
```

Fig. 6A

```
331 L LN E P K W G H L R E L H R A I K Q C E S A L V S V D P T   LEG11CON.pro
323 L L R Q P K W G H L K D L H R A I K L C E P A L V S G D P A   CONTIG.TEG1.PRO 361 V S W P G K N L E V H L Y K T E S A - C A A F L A N Y N T D   LEG11CON.pro
353 V T A L G H Q Q E A H V F R S K A G S C A A F L A N Y D O H   CONTIG.TEG1.PRO 390 Y S T Q V K F G N G Q Y D L P P W S I S I L P D C K T E V F   LEG11CON.pro
383 S F A T V S F A N R H Y N L P P W S I S I L P D C K N T V F   CONTIG.TEG1.PRO 420 N T A K V N S P R L H R K M T P V N S A F A W Q S Y N E E P   LEG11CON.pro
413 N T A R I G A Q S A O M K M T P V S R G L P W Q S F N E E -   CONTIG.TEG1.PRO 450 A S S E N D P V T G Y A L W E Q V G V T R D S S D Y L W Y    LEG11CON.pro
442 T S S Y E D S S F T V V G L L E O I N T T R D V S D Y L W Y  CONTIG.TEG1.PRO 480 L T D V N I G P N D - - I K D G K W P V L T A M S A G H V L   LEG11CON.pro
472 S T D V K I D S R E K F L R G G K W P W L T I M S A G H A L   CONTIG.TEG1.PRO 508 N V F I N G Q Y A G T A Y G S L D D P R L T F S Q S V N L R   LEG11CON.pro
502 H V F V N G Q L A G T A Y G S L E K P K L T F S K A V N L R   CONTIG.TEG1.PRO 538 V G N N K I S L L S V S V G L A N V G T H F E T W N T G V L   LEG11CON.pro
532 A G V N K I S L L S I A V G L P N I G P H F E T W N A G V L   CONTIG.TEG1.PRO 568 G P V T L T G L S S G T W D L S K Q K W S Y K I G L K G E S   LEG11CON.pro
562 G P V S L T G L D E G K R D L T W Q K W F Y K V G L K G E A   CONTIG.TEG1.PRO 598 L S L H T E A G S N S V E W V Q G S L V A K K Q P L A W Y K   LEG11CON.pro
592 L S L H S L S G S P S V E W V E G S L V A Q K O P L S W Y K   CONTIG.TEG1.PRO 628 T T F S A P A G N D P L A L D L G S M G K G E V W V N G Q S   LEG11CON.pro
622 T T F N A P D G N E P L A L D M N T M G K G O V W I N G Q S   CONTIG.TEG1.PRO
```

Fig. 6B

```
658  I G R H W P G N K A R G N C G N C N Y A G T Y T D T K C L A    LEG11CON.pro
652  L G R H W P A Y K S S G S C S V C N Y T G W F D E K K C L T    CONTIG.TEG1.PRO 688  N C G Q P S Q R W Y H V P R S W L R S G G N Y L V V L E E W    LEG11CON.pro
682  N C G E G S Q R W Y H V P R S W L Y P T G N L L V V F E E W    CONTIG.TEG1.PRO 718  G G D P N G I A L V E R T .                                    LEG11CON.pro
712  G G D P Y G I T L V K R E I G S V C A A D I Y E W Q P O L L N  CONTIG.TEG1.PRO 731  W Q R L V S G K F D R P L R P K A H L K C A P G Q K I S S I    CONTIG.TEG1.PRO 731  K F A S F G T P E G V C G N F Q Q G S C H A P R S Y D A F K    CONTIG.TEG1.PRO 731  K N C V G K E S C S V Q V T P E N F G G D P C R N V L K K L    CONTIG.TEG1.PRO 731  S V E A I C S                                                  CONTIG.TEG1.PRO
```

Fig. 6C

EXO-(1→4)-β-D GALACTANASE

This application claims benefit of international application PCT/GB95/00372, filed Feb. 23, 1995.

FIELD OF THE INVENTION

This invention relates to novel nucleotide sequences and to vectors and hosts comprising said sequences. The invention also relates to a method of altering the characteristics of plants.

BACKGROUND OF THE INVENTION

Pectin is a major matrix polysaccharide found in the cell wall of plants. Pectins are composed of two distinct regions. The smooth region comprises of long stretches of homogalacturonan interrupted by rhamnose, and is relatively unbranched. The hairy region is rich in galacturonic and rhamnose residues and is highly branched. The side branches contain different sugars but primarily comprise the neutral sugar side chains, arabinan, β-(1→4)-galactan and arabinogalactan. The function of these neutral sugar polysaccnaride side chains has not been fully established. It is speculated that they may function in modulating the pore size of the cell wall and therefore the mobility of proteins, possibly restricting access of various enzymes to their substrates. Moreover, the interaction of the side chains between themselves and with other cell wall polymers could contribute to the structure of the cell wall and the rheoiogical properties of products derived from them. In vitro studies carried out on a solution of apple pectin with different neutral sugar contents demonstrate that increase in branching of pectin results in higher zero-shear viscosity. It was concluded that this was due to pectin side chain interactions. In addition, more branched pectin gives higher elastic or storage moduli (G') than less branched pectin, suggesting that side chain of pectins contribute to elastic properties (Hwang et al., (1993) Food Hydrocolloids 7, 39–53).

The hydrolysis of β-(1→4)-linked galactose from polymeric galactan side chains of pectin has been demonstrated in different plants and in various physiological states (de Vetten and Huber (1990) Physiol. Plant. 78, 447–454; Fischer and Bennett (1991) Ann. Rev. Plant Physiol Plant Mol. Biol. 42, 675–703). During the process of fruit ripening, the loss of the neutral sugar, galactose, is the single most extensive change in the cell walls of many fruits (Fischer and Bennett 1991). Galactose mobilization during fruit ripening has been demonstrated in several fruits including tomato, hot pepper, strawberry, apple, coffee, muskmelon, kiwi fruit, and nectarines. During the senescence of carnation petals, the decrease in cell wall yield is due largely (45%) to a loss of the neutral sugar galactose (de Vetten and Huber 1990). In germinating lupin cotyledons, up to 80% of galactose is mobilized primarily from the β-(1→4)-linked galactan side chains of the rhamnogalacturonan backbone from secondary cell walls adapted to a storage function. A β-galactosidase (exo-(1→4)-β-D-galactanase) would be the enzyme activity predicted to be responsible for galactose mobilization from the galactan side chains of pectin.

β-Galactosidase enzvme activities (including exogalactanase activities) in plants have been described in the prior art (Dick et al., (1990) Physiol. Plant. 89, 369–375; Burns (1990) Phytochemistry 29, 2425–2429; Singh and Knox. (1985) Phytochemistry 24, 1639–1643; Kundu et al., (1980) Phytochemistry 29, 2079–2082). The purification of some β-galactosidase enzymes has been described, though in many instances synthetic substrates rather than endogenous substrates have been used for enzvme characterization (Ogawa et al., (1990) Nippon Shokuin Kogyo Gakkaishi 37, 298–305; Giannakouros et al., (1991) Physiol. Plant. 82, 413–418). There is evidence that plant β-galactosidases may be associated with developmental processes requiring cell wall turnover, like tissue elongation in *Cicer arietinum* epicotyl segments. In this tissue, β-galactosidase has been demonstrated to he responsible for autolysis, and the natural substrate of the autolytic reaction is the pectic fraction of the cell wall (Dopico et al., (1989) Physiol. Plant. 75, 458–464; Valero and Labrador (1993) Physiol. Plant. 89, 199–203). A β-galactosidase has been highly purified from the buffer-soluble fraction of carrot cell culture homogenate (Konno et al., (1986) Physiol. Plant. 68, 46–52). The enzyme was active on β-(1→4)-linked galactan prepared from citrus pectin in an exo fashion. The loss of galactose in cell walls during softening has been widely documented (Bartley (1974) Phytochemistry 13, 2107–2111; Redgewell et al., (1992) Plant Physiol. 98, 71–81; Wegrzyn and MacRae (1992) Hort. Sci. 27, 900–902). In tomato, it has been found that the increase in monomeric galactose during fruit ripening is due to an increase in the rate of galactose solubilization from the cell wall rather than changes in the rate of metabolic utilization of the solubilized galactose (Kim et al., (1991) Postharvest Biol. Technol. 1, 67–80). This suggests the action of β-galactosidases in vivo during fruit ripening. There have been several reports of increased β-galactosidase activity during the process of fruit ripening (Bartley 1974; Pressey (1983) Plant Physiol. 71, 132–235; Ross et al., (1993) Planta 1889, 499–506). The β-galactosidase purified from kiwifruit was active in cleaving terminal galactose attached at either the 2, 3, 4 or 6 position (Ross et al., 1993). In tomato fruits, Gross and Wallner (1979, Plant Physiol. 63, 117–120) have shown that decline in wall galactans precedes or accompanies increase in soluble polyuronide. Pressey (1983) has characterized three β-galactosidase activities in ripening tomato fruits of which one (β-galactosidase II), increases 3-fold during ripening. This enzyme was also able to degrade galactan extracted from the cell walls of green tomato and the author suggests a possible role for it in tomato softening. A β-galactosidase has been purified from ripe coffee beans which increases four fold during the transition from immature to ripe fruits (Golden et al., (1993) Phytochemistry 34, 355–360). The enzyme displayed activity against galactan and arabinogalctan, however pectin yielded galactose only in conjunction with an endopolygalacturonase activity.

Solubilization of pectin during fruit ripening is a well-documented phenomenon (Fischer and Bennett, 1991). The action of endopolygalacturonase was considered to be the most likely cause of pectin solubilization, which was thought to be the cause of softening of fruits. Recent studies in transgenic tomato fruits argue against PG being the sole causal agent in the process of fruit softening (Giovannoni et al., (1989) Plant Cell 1, 53–63; Smith et al., (1990) Plant Mol. Biol. 14, 369–379). Recent evidence in fruits with no apparent endo or exo polyalacturonase activity suggests a role for β-galactosidases active on the galactan side chains for the solubilization of pectin (Cutillas-Iturralde el al., (1993) Physiol. Plant. 89, 369–375). Ranawala et al., ((1992) Plant Physiol. 100, 1318–1325) have described a NaCl-released β-galactosidase activity from cell walls of ripe muskmelon (*Cucumis melo*) fruits, that has the ability to degrade (in vitro) pectin extracted from pre-ripe fruits to smaller sizes of pectin, similar to those observed in ripe fruits. Moreover, there is no detectable PG activity at any stage of muskmelon fruit development and ripening. De Veau et al., (1993 Physiol. Plant. 87, 279–285) have demonstrated increased pectin solubility and decreased apparent molecular weight of pectin extracted from mature green tomato fruits when digested in vitro with β-galactosidases isolated from avocado fruits. Though tomato pectin has been shown to contain at least 10% galactose, only 0.2% was mobilized using avocado derived β-galactosidases. However, this minor change in pectin galactose composition was sufficient to change the solubility of polymeric pectin. These results suggest that an exo-galactanase might play an important role in the pectin solubilization during the process of fruit ripening.

For all the β-galactosidase activities so far described, there are only some indications as to which of the macromolecular components of the cell walls are the actual in vivo substrates. An exception is the β-galactosidase isolated from germinating nasturtium (*Tropaeolum majus*) cotyledons. The enzyme activity is coincident with xyloglucan mobilization, and the purified enzyme has the unique capability of hydrolysing the terminal β-1,2-linked galactose from the galactoxylosyl sidechain of the xyloglucan polymer (Edwards et al., (1988) J. Biol. Chem. 263, 4333–4337). Buckeridge and Reid recently described (in the printed abstracts of disclosures made at the 6$^{th}$ Cell Wall Meeting, Nijmegen, Aug. 25–28, 1992, and at the Scottish Cell Wall Group Meeting, April 1993) the purification of a β-galactosidase (an exo-(1→4)-β-D-galactanase) that metabolises the linear β-(1→4)-galactan component of the lupin cotyledonary cell wall. This enzyme is thought to play a key role in the post germinative mobilization of galactan. The enzyme activity is detectable only when galactan mobilization begins, increases during the period of galactan mobilization, and subsequently declines. The changes in exo-galactanase enzyme activity have been shown to correlate with changes in the level of the exo-galactanase enzyme, as determined by immunoblotting. This enzyme is highly specific to β-(1→4)-galactan and does not hydrolyse other plant cell wall polysaccharides known to have terminal non-reducing galactose residues, like nasturtium xyloglucan (terminal (1→2)-β-linked galactose) and larch arabinogalactan (terminal non-reducing (1→3) and (1→6) linked galactose residues.

The enzyme, exo-(1→4)-β-D-galactanase, (which catalyses the hydrolysis of terminal galactose residues from (1→4)-β-linked galactan side chains) appears to have an important role during several physiological processes. The present inventors have achieved the partial protein sequencing, cloning and sequence analysis of a full length cDNA coding for the exo-(1→4)-β-D-galactanase from germinating agricultural lupins (*Lupus angustifolius*).

SUMMARY OF THE INVENTION

In a first aspect the invention provides a nucleotide sequence comprising substantially nucleotides 229 to 2319 of the sequence (Seq ID No. 1) shown in FIG. 1 encoding an enzyme having exo-(1→4)-β-D-galactanase activity, or a precursor or derivative of such an enzyme, or the functional equivalent of such a nucleotide sequence.

For the purposes of the present specification, a precursor shall be understood to mean a polypeptide (active or inactive), which is longer than that encoded by nucleotides 229 to 2319 of the sequence shown in FIG. 1, which can be processed (e.g by proteolysis) in vitro or, more preferably, in vivo, to yield an active enzyme. A derivative shall be understood to mean a polypeptide, obtained by processing in vitro or in vivo, having enzyme activity, which is shorter than that encoded by nucleotides 229 to 2319 of the sequence shown in FIG. 1. Particularly preferred derivatives are those having molecular weights of about 60 kDa and 45 kDa (as determined by SDS-PAGE), which are formed either by intracellular C-terminal cleavage of the polypeptide encoded by nucleotides 229 to 2319 of FIG. 1, or which arise during purification of the enzyme.

Preferably the nucleotide sequence of the invention comprises a 5' ATG start signal. It is also preferred that the sequence further comprises a suitable 5' untranslated region, including a promoter, to enable expression in appropriate host cells. It is also preferred that the sequence comprises signals to optimise expression in appropriate host cells, such as 3' polyadenylation signal to optimise expression in eukaryotes. The sequence of the invention may also comprise a sequence encoding a signal peptide. Particularly preferred embodiments are those sequences which comprise substantially the nucleotide sequence corresponding to nucleotides 163 to 228, or 151 to 228, or 130 to 228 of the sequence shown in FIG. 1.

The term "functional equivalent" as used herein, is intended to refer to those sequences which differ from the precise nucleotide sequence in FIG. 1. In particular, the term refers to; those nucleotide sequences which encode the same amino acid sequence as that encoded by the sequence shown in FIG. 1 but which, by virtue of the degeneracy of the genetic code, possess a different nucleotide sequence; sequences which encode substantially the same polypeptide but wherein there may be one or more conserved amino acid substitutions (i.e. the substitution of one amino acid for another with similar properties). A functionally equivalent sequence will generally encode a polypeptide exhibiting at least 70%, amino acid homology, preferably at least 75%, and more preferably at least 85% amino acid homology with the amino acid sequence encoded by nucleotides 229 to 2319 shown in FIG. 1. Accordingly, preferred functionally equivalent sequences will be able to hybridise with the complement of the sequence shown in FIG. 1 under standard hybridisation conditions (e.g. such as described by Sambrook et al., 1989), but preferably under more stringent conditions.

A particular example of functional equivalents are those sequences which are substantially the antisense equivalent of nucleotides 229 to 2319 of the sequence of FIG. 1. Such sequences are therefore able to hybridise with the sequence shown in FIG. 1. Preferably such antisense equivalents are able to interfere with the expression of the sense sequence, at the DNA and/or mRNA level.

One functional equivalent to the nucleotide sequence of the invention is the nucleotide sequence comprising substantially nucleotides 117 to 2555 of the sequence (Seq ID No. 18) shown in FIG. 5, which encodes a mature exo-galactanase obtainable from tomato fruit. Also included within the scope of the invention are those nucleotide sequences encoding precursors of the mature enzyme, such as nucleotide sequences comprising substantially nucleotides 42 to 2555 of the sequence shown in FIG. 5. It will be apparent to those skilled in the art that other nucleotide sequences may exist which encode substantially the same amino acid sequence as that of the polypeptide shown in FIG. 5 but which, by virtue of the degeneracy of the genetic code, possess a different nucleotide sequence to that shown in FIG. 5. Such obvious variants are to be considered as functional equivalents falling within the scope of the invention.

In a second aspect the invention provides a polypeptide having exo-(1→4)-β-D-galactanase activity and comprising substantially the amino acid sequence encoded by nucleotides 229 to 2319 of the sequence shown in FIG. 1, or a precursor or derivative of such a polypeptide, or a functional equivalent thereof.

A particular functionally equivalent polypeptide is that encoded by nucleotides 117 to 2555 of the sequence shown in FIG. 5, or a precursor or derivative thereof. One such precursor comprises, for example, the polyeptide encoded by nucleotides 42 to 2555 of the sequence shown in FIG. 5.

In a third aspect the invention provides a vector comprising substantially the sequence of nucleotides 229 to 2319 of the sequence shown in FIG. 1, or a functional equivalent thereof. Preferably the vector is capable of directing the expression of a polypeptide having exo-(1→4)-β-D-galactanase activity in an appropriate host, or is capable (directly or indirectly) of interfering with the expression of such a polypeptide.

Transformation techniques for introducing the sequence of the invention into various hosts are well-known to those skilled in the art. Accordingly, in a fourth aspect the invention provides a host or host cell into which the sequence of the invention (or a functional equivalent thereof) has been artificially introduced. Preferably the host or host cell is a plant or plant cell, although other hosts could be employed. For example, if one wished to express large quantities of the enzyme, one could introduce the sequence of the invention into a yeast cell. Possible uses of such a purified, recombinant enzyme include the following: modification, degradation or liquefaction of plant materials in order to affect (a) mechanical properties relating to eating texture; (b) particle sizes of, for example, fruit or vegetable juices (affecting haze); or (c) extractability of colors, flavours or vitamins.

As will be clear to those skilled in the art, because of the role exo-(1→4)-β-D-galactanase plays in breaking down polymers present in the plant cell wall, altering (increasing or decreasing) the levels, or altering the pattern, of expression of this enzyme in a plant might have an effect on certain characteristics of the plant. In particular, one might expect to be able to alter; growth, texture or ripening of the plant or part thereof.

In a fifth aspect, the invention provides a method of altering the characteristics of a plant or part thereof, comprising introducing into the plant the sequence of the invention or a functional equivalent thereof, so as to alter the level or pattern of exo-(1→4)-β-D-galactanase activity in the plant.

If the sequence introduced into the plant is in the sense orientation relative to the promoter, it may result in increased levels of expression. Conversely, introduction into a plant of a sequence in the antisense orientation relative to the promoter may result in a reduction of levels of expression. The plant into which the sequence is introduced is preferably a commercially significant plant in which molecules comprising (1→4)-β-D-linked galactanase residues perform a structural role. Examples of such plants include: alfalfa, apple, broccoli, cabbage, carrot, cauliflower, celery, cranberry, cucumber, eggplant, flax, grape, horseradish, kiwi, lettuce, mangoes, melon, oilseed rape, papaya, pea, peaches, pears, peppers, plum, potato, raspberry, soybean, strawberry, suzarbeat, sweet potato, tobacco, tomato and walnut.

With the knowledge of the sequence data disclosed herein, those skilled in the art will appreciate that it should prove possible to clone functionally equivalent sequences (as defined above) from other plants. Accordingly, in a further aspect the invention provides a method of isolating a functionally equivalent sequence, comprising isolating mRNA from a plant of interest and screening (by means of hybridisation or PCR) the cDNA obtained therefrom using a probe nucleic acid sequence which is substantially complementary to at least part of the sequence shown in FIG. 1.

BRIEF DESCRIPTION OF THE DRAWINGS

The invention will now be described by way of example and with reference to the drawings, of which:

FIG. 1 shows the nucleotide sequence (Seq ID No. 1) of the invention together with the amino acid sequence (Seq ID No. 2) of the polypeptide encoded by the nucleotide sequence;

FIG. 2 shows the N-terminal amino acid sequence data obtained by peptide sequencing of the 60, 45 and 15 kDa lupin polypeptides that co-purify during enzyme purification (Seq ID No.s 3–5 respectively);

FIG. 3 shows the N-terminal amino acid sequence data for the 60 kDa lupin exo-galactanase SEQ ID No. 3 together with the nucleotide sequence of EXO1 (Seq ID No. 6), the probe used to screen the cDNA library;

FIG. 4 shows a comparison between the cDNA-encoded polypeptide sequences of lupin exo-galactanase (SEQ ID No. 2) and that encoding a protein of unknown function (SEQ ID No. 20) from carnations (which sequence is already found in publicly available databases);

FIG. 5 shows the cDNA sequence (Seq ID No. 18) of a functionally equivalent enzyme from tomato, together with the amino acid sequence (Seq ID No. 19) of the polypeptide encoded thereby; and FIG. 6 shows a comparison of the amino acid sequences of the lupin (SEQ ID No. 2) and tomato (SEQ ID No. 19) enzymes; the tomato polypeptide sequence is shown boxed and those portions of the lupin polypeptide which possess an identical sequence are also boxed.

EXAMPLES

SDS-PAGE and Electroblotting for N-terminal Sequence Analysis:

The lupin exo-galactanase enzyme was purified from 18-days after planting (dap) lupin cotyledons as described (Buckeridge and Reid 1993, abstracts described previously), and supplied by Dr. J. S. Grant Reid (University of Stirling). The protein preparation was composed of a major protein (60 kDa), and two minor proteins (45 kDa and 15 kDa) when analyzed on SDS gels. SDS-PAGE was performed by the method of Laemmli (1970, Nature 227, 680–685) on linear 10% (w/v) acrylamide slab gels on a BioRad electrophoresis kit. Proteins were electroblotted onto the PROBLOTT™ membrane (Applied Biosystems, Warrington, U.K.) as described by Matsudaira (1987) with the following adaptations. Gels were pre-run with 50 μM glutathione (Sigma) added to the cathode electrode buffer. Sodium thioglycolate (0.1 mM, Sigma) was added to fresh cathode buffer for sample electrophoresis. Protein was stained with Coomassie brilliant blue following Applied Biosystem's recommendations.

Endoproteinase Lys-C Digestion:

A preparation containing approximately 50 μg purified enzyme (800 pmoles intact exo-galactanase) was brought to pH 8.5, measured with indicator paper, using 1M Tris/HCl pH 8.5. The sample was boiled for 5 min to denature the protein. Endoproteinase Lys-C (Sequencing grade: Boehringer Mannheim) was added at a ratio of 1:50 w/w. The incubation was left at 37° C. overnight and stored at −20° C. prior to reversed-phase chromatography.

HPLC Separation of Peptides:

Reversed-phase chromatography was performed at 30° C. on Applied Biosytems model 130A HPLC separation system. Samples were loaded, via a 500 µl loop onto a Brownlee RP 300-C8 microbore column (250×1 mm id: 7µ) pre-equilibrated in 0.1% (v/v) TFA. Flow rate was 0.1 ml min$^{-1}$. Peptides were eluted with a gradient of increasing buffer B (90% acetonitrile: 0.085% TFA) 0–70% over 70 minutes. Absorbance was monitored at 214 nm and peaks were collected manually into Eppendorf tubes with a time delay to allow for the dead space between the detector and outlet. Fractions were stored at −20° C. Prior to loading sample onto the HPLC, acetonitrile gradients were performed until a reproducible low baseline was obtained.

Protein Sequencing:

This was performed on the Applied Biosystems model 475 protein sequencer.

At the stage of protein purification (18 d.a.p), the exo-galactanase enzyme was purified as a 60 kDa protein, along with a 45 kDa and a 15 kDa protein that co-purifies with it. The N-terminal amino acid sequence of these three polypeptides is illustrated in FIG. 2 (Seq ID No.s 3–5). The Figure shows that the 60 and 45 kDa proteins have an identical N-terminal sequence suggesting that they are derived by C-terminal cleavage of the same parent molecule. Antiserum raised against and affinity purified on the 60 kDa protein recognises larger proteins (~80 kDa) at earlier stages of seed germination. It is possible that the purified enzyme (60 kDa) is proteolytically derived from a larger precursor. This is evident from the observation that the deduced protein coded for by the purified cDNA, has a molecular weight of ~77 kDa. The C-terminal cleavage could occur in vivo or during the process of protein purification. The 60 kDa polypeptide clearly retains activity and is regarded as a functionally equivalent derivative of the sequence of the invention. The 45 kDa polypeptide may possess activity (this has not yet been investigated) and, if so, would also be regarded as a functionally equivalent derivative of the sequence of the invention.

mRNA Isolation and cDNA Library Synthesis:

12 d.a.p lupin cotyledons were supplied by Dr. Reid (Univ of Stirling). Total RNA was extracted using Qiagen columns according to manufacturers recommendations, with some modifications. Total RNA was extracted in two batches. In each batch, 1.5 g of 12 d.a.p lupin cotyledons was ground to a fine powder under liquid nitrogen and distributed to six tubes, each containing 3 mls of cold extraction buffer (4M Guanidine thiocyanate, 100 mM Tris HCl pH7.5, and 25 mM EDTA). To this was added 3 µl of β-mercaptoethanol and 240 µl of 25% Triton X-100 and the mix was incubated on ice for 15 min, 3 mls of cold 3 M Sodium acetate pH6 was added and incubation on ice continued for a further 15 min. The homogenate was centrifuged at 15,000×g for 30 min at 4° C. 5 mls of cold iso-propanol was added to the supernatant and incubated on ice for 5 min. The precipitate was concentrated by centrifugation at 15,000×g for 30 min at 4° C. The pellet was resuspended in 8 ml of cold TE (20 mM Tris HCl pH8, 1 mM EDTA), and undissolved particles were removed by an additional centrifugation at 20,000×g for 15 min at 4° C. 2 ml of S1 (2M NaCl and 250 mM MOPS pH7) was added to the supernatant, which was then applied to a Qiagen-tip 100 column pre-equilibrated with 3 ml of buffer QAT (0.4M NaCl, 50 mM MOPS pH7.0, 15% ethanol and 0.15% Triton X-100). Each column was then washed with 15 ml of buffer QA (0.4M NaCl, 50 mM MOPS pH7.0, and 15% ethanol). Total RNA was eluted with 7.5 ml of buffer QRU (0.9M NaCl, 50 mM MOPS pH7.0, 15% ethanol and 6M Urea), precipitated with an equal volume of iso-propanol for 10 min on ice and centrifuged at 15,000×g for 30 min at 4° C. The pellet was washed once in 80% ethanol, air dried and dissolved in a total of 1.5 ml. All the fractions were pooled at this stage and the yield of total RNA quantified spectrophotometrically at O.D$_{260}$.

Messenger RNA was fractionated from 1.2 mgs of lupin total RNA by affinity chromatography on oligo(dT) cellulose, using Poly (A$^+$) Quik columns from Stratagene according to manufacturers instructions, 5 µg of poly (A$^+$) RNA was used to synthesize a directional cDNA library using a ZAP cDNA synthesis kit (Stratagene) and packaged using Gigapack II Gold™ packaging extract (Stratagene) according to manufacturers instructions. The packaged library had a titre of approx 1×10$^6$ pfu of which 4.8×10$^4$ pfu were screened in duplicate.

Design of Oligonucleotide Probe:

A stretch of 8 amino acids (shown underlined and in bold type in FIG. 3a) within the N-terminal peptide sequence of the mature lupin exo-galactanase enzyme was used to design an oligonucleotide probe (EXO1, shown in FIG. 3b, Seq ID No. 6) for the screening of the cDNA library. The oligonucleotide was 23 nucleotides long with a degeneracy of 48 and incorporated one inosine at a wobble base position. The oligonucleotide probe was designed to be complementary to the mRNA coding for the lupin exo-galactanase.

cDNA Library Screening:

Screening of the lupin cDNA library was essentially as described in the ZAP cDNA synthesis and cloning protocol (Stratagene). A total of 4.8×10$^4$ plaque forming units (pfu) were plated on four LB (Luria-Bertani) agar plates, using the Sure™ strain of *Escherichia coli* bacteria (Stratazene), and incubated for 16 h at 39° C. The plates were then chilled for 2 hr at 4° C. and plaque lifts were made in duplicate onto 150 mm nitrocellulose filters (SS) as described (Sambrook et al., (1989) Molecular Cloning, A Laboratory Manual. 2$^{nd}$ edition, Cold Spring Harbor Laboratory Press). Following denaturation and neutralization, the filters were baked at 80° C. for 2 hrs. The filters were incubated in 30 mls of pre-hybridization solution (6×SSC, 5× Denhardts, 100 µg/ml salmon testis DNA, and 0.5% SDS) at 42° C. for 4 hrs with gentle agitation, 15 pmol of oligonucleotide EXO1 was end labelled using gamma-$^{32}$-P ATP with polynucleotide kinase as described (Sambrook et al. 1989). Labelled oligonucleotides were separated from the unincorporated radioactive nucleotides by passage through a P-50 column, and added to the pre-hybridization solution at a concentration of 2×10$^5$ cpm/ml. Hybridization was carried out for 18 hrs with gentle shaking at 42° C., following which the filters were washed briefly (1–2 mins) in two changes of 6×SSC, wrapped in saran-wrap, and exposed to x-ray film (Kodak™ LS); Autoradiography was carried out for 16 hrs at −80° C. in cassettes with intensifying screens. Positive plaques were identified by autoradiography and the plaques picked into SM. 12 positive clones were taken through an additional round of screening to plaque purity. An estimate of the abundance of the mRNA coding for the lupin exo-galactanase cannot be made based on these results as the probe used (designed to the N-terminal peptide sequence), would be expected to detect only full length cDNAs. Following the second round of screening, 6 plaque pure positives were isolated, and in vivo excised.

In Vivo Excision:

Positive clones were in vivo excised with the Bluescript™ phagemid from the Uni-Zap XRT™ vector as described in the manufacturers protocol (Stratagene), plasmid preparations of the isolated clones were made using Qiagen P-100 tip columns as recommended by the manufacturer. Clones were further investigated by PCR (polymerase chain reaction) and by restriction analysis, 5 of the 6 isolated clones were successfully amplified using EXO 1 and a vector-based primer for amplification in the PCR. The 5 clones all possessed an insert of similar size (~2,600 bp) which was released upon digestion of the purified Bluescript plasmid with the restriction enzymes Eco RI and Xho I, as determined by agarose gel electrophoresis.

Sequence Determination:

The cDNA isolated by screening the lupin cDNA library using the oligonucleotide EXO 1 was analyzed by sequencing the double stranded plasmid using appropriate primers by Taq Dye-Deoxy™ terminator chemistry and analyzed on the automated ABI 373A DNA sequencer.

Sequence Analysis:

The isolated cDNA clone (Seq ID No. 1, shown in FIG. 1) is 2628 bp long and includes a 30 bp poly A tail. The longest open reading frame (2190 bp, upper case letters) codes for a 730 amino acid polypeptide (Seq ID No. 2, 81.6 kDa, shown above the nucleotide sequence in single letter code) and includes a 33 amino acid putative signal peptide. However, there are three additional possible start sites between the first start (ATG) codon and the N-terminal of the mature protein which would reduce the signal peptide to either 26, 22 or 15 amino acids. The first three start sites all precede the hydrophobic core that is located within the signal peptide. The mature enzyme is coded for by 697 amino acids with a molecular weight of ~77 kDa. As previously mentioned, the antibody raised against the ~60 kDa protein cross reacts with a larger protein (~80 kDa), and this might serve as a precursor to the 60 kDa protein by cleavage at the C-terminal end, as the N-terminal sequence of the 60 kDa band and the mature enzyme (deduced from the cDNA) are identical. The serine (underlined) at residue 34 marks the start of the amino acid sequence of the mature protein, the deduced sequence immediately C-terminal of this corresponding to the amino acid sequence actually determined by protein sequencing. The N-terminal of the small (~15 kDa) protein has been located within the deduced amino acid of the cDNA, and cleavage at this point would release a 12.5 kDa protein, confirming that this molecule is derived by the cleavage of the C-terminal of the synthesized protein. All the peptide sequences derived by protease digestion and sequencing of the enzyme (peptide sequence data obtained include the following: VAKKQPLAWYKTT, FSAPAGNDPL, GEVWVNGQSIG, and GNCGNCNYAGTYTDTK, Seq ID No.s 7–10 respectively) have been located within the deduced amino acid sequence of the cDNA, further confirming the identity of the cDNA as the one coding for the lupin exo-galactanase. Whether the synthesized enzyme is specifically cleaved in vivo or whether cleavage occurs during the purification process is open to speculation.

Homology to Other Sequences:

The lupin exo-galactanase shows high homology to at least one other sequence. At the amino acid level, it has a 66.5% identity over a 717 amino acid overlap with the deduced amino acid sequence of a highly expressed ethylene regulated gene with unknown function isolated from senescing carnation petals (Raghothama et al., (1991) Plant Mol. Biol. 17, 61–71). This level of amino acid homology is insufficient for the sequence to he considered as a functional equivalent of the lupin exo-galactanase. A comparison between the two polypeptide sequences is shown in FIG. 4, the carnation sequence (CARS12.pro) above the lupin sequence (LEG11CON.pro). Comparison of these two sequences reveals a number of peptides (shown in boxes) which might well be conserved amone enzymes of this type. It is suggested that functional equivalents of lupin exo-galactanase which exhibit a higher degree of homology than that shown by the carnation polypeptide may also comprise these or similar peptide sequences.

Isolation of exo-galactanase cDNAs from Other Plants

With knowledge of the sequence of the exo-galactanse from lupins, it should prove possible for those skilled in the art to isolate functionally equivalent cDNAs from other plants. Described below is a method which could potentially be used for this purpose.

The cDNA coding for the lupin exo-galactanase will be used to isolate functional homologues from other plants (e.g. tomato). The lupin cDNA will be radiolabelled and used as a probe to screen a cDNA library constructed from mRNA isolated from the plant of interest. About $3 \times 10^4$ pfu will be plated on each LB-agarose plate (as described previously) and filters will be probed with the radiolabelled full-length lupin exo-galactanase cDNA. The hybridisation solution will be as described above, but the temperature of hybridisation will be reduced to about 50° C. The lower temperature is necessary because a heterologous probe (i.e. lupin cDNA) will be used to screen the cDNA library. The hybridised filters will be washed in 2×SSC at room temperature for 20 minutes and exposed to x-ray sensitive films. Putative positive clones will be plaque purified and sequence-analysed for homology with the lupin exo-galactanase cDNA. The example below illustrates how this procedure was used to isolate cDNA clones encoding an exo-galactanase from tomato fruits which is functionally equivalent to that obtained from lupin.

Purification of a Polypeptide from Tomato with exo-galactanase Activity

Step 1: Assay for Activity of exogalactanase

Exo-galactanase activity in various tomato fruit extracts was measured by the release of free galactose from galactan isolated from lupin seed. Each assay contained the following components: 30 $\mu$l of a 1% galactan solution, 15 $\mu$l 1M ammonium acetate pH 5.0 containing 0.1% sodium azide and up to 30 $\mu$l tomato extract depending on enzyme activity. Assays were incubated at 30° C. for 17–24 hours and terminated by boiling the solution for 2 min. Aliquots (64 $\mu$l) were used for determination of galactose using $\beta$-D-galactose dehydrogenase essentially as described by Kurz and Wallenfels (1974. In "Methods of enzymatic analysis", pp1279–1282. Verlag, Chemie, Weinheim).

Step 2: Extraction of exogalactanase from Tomato Pericarp

It was found that exo-galactanase activity could be efficiently extracted from tomato fruit pericarp by 0.2M sodium phosohate buffer, pH 7.2

Step 3: Choice of Starting Material for Purification

Crude extracts were made (in 0.2M sodium phosphate buffer, pH 7.2) from tomato pericarp (*Lycopersicum esculentum*, var. Moneymaker) tissues taken from various stages of growth and ripening. It was found that pink and red fruit had the highest exogalactanase activity, whether expressed as total or specific activity. Therefore the pericarp of red fruit was used as the starting material for purification.

Step 4: Ammonium Sulphate Precipitation

Pericarp tissue (500 g) from red fruit was harvested, frozen in liquid nitrogen, and stored at −20° C. The tissue was homogenised in 1 g:1.5 vol 0.2M sodium phosphate, pH 7.2 with 1.0% (w/v) insoluble PVP (polyvinyl pyrrolidone) in a blender. The homogenate was stirred for 1 hour at 4° C. to allow diffusion of cell wall enzymes into the extraction buffer. Insoluble material was removed by centrifugation at 20,000×g, 10 min. 4° C. in the SS34 rotor of the Sorvall RC5B centrifuge. The supernatant was passed through glasswool, and brought to 30% ammonium sulphate saturation by addition of solid ammonium sulphate (16.4 g/100 ml). The mixture was stirred for 40 min at 4° C., and the precipitated proteins were removed by centrifugation (30,000×g, 20 min, 4° C.). The supernatant was brought to 70% ammonium sulphate saturation by addition of solid ammonium sulphate (24.9 g/100 ml). The mixture was stirred for 40 min at 4° C., and the precipitated proteins collected by centrifugation (30,000×g, 20 min, 4° C.). The ammonium suldhate precipitated proteins were stored at −20° C. without resuspension.

Step 5: DE52 Chromatography

30–70% ammonium sulphate precipitated proteins were resuspended in 48 ml of 20 mM Tris/HCl, pH 7.8 (Buffer A) and dialysed overnight against 4.5 L of Buffer A. The sample was centrifuged at 30,000×g for 10 min, 4° C. and loaded onto a 40 ml DE52 column (Whatman), equilibrated in Buffer A. at 0.5 ml/min. The column was washed with Buffer A (flow rate 1.0 ml/min) until all unbound proteins were removed. Bound proteins were eluted with a 0–100% gradient of Buffer B (as Buffer A. but with 1M NaCl) over 6 column volumes. Fractions (2 ml ) were collected and assayed for exo-galactanase activity. Fractions containing high exo-galactanase activity were either dialysed immediately as detailed below or stored at −20° C.

Step 6: Mono P Chromatography

Fractions pooled from DE52 chromatography were dialysed overnight against 4.5 L of 0.025M triethanolamine/iminodiacetic acid pH 8.3 (Buffer C). The dialysed sample was centrifuged and the supernatant loaded via a 50 ml superloop onto a Mono P column (Pharmacia HR 5/20), equilibrated in Buffer C, at a flow rate of 1 ml/min. The column was washed in Buffer C until all unbound proteins were removed. Bound proteins were eluted from the column with 50 ml 10% (v/v) polybuffer 7/4, pH 4.8/iminodiacetic acid, at a flow rate of 1 ml/min. Fractions (0.5 ml) were collected and assayed for exo-galactanase activity. Fractions containing activity which eluted early in the pH gradient (approx pH 8.0) were pooled and dialysed overnight against 50 mM ammonium acetate pH 5.0 (Buffer D).

Step 7: Lactose Agarose Chromatography

Dialysed sample was loaded onto a 5 ml lactose agarose (Sigma) column, equilibrated in Buffer D, at a flow rate of 0.13 ml/min. The column was washed with Buffer D to remove unbound proteins. Bound proteins were eluted from the column with 0.1M Tris/HCl pH 8.6/0.2M NaCl. Fractions (0.5 ml) were collected and assayed for exo-galactanase activity.

Step 8: N-terminal amino acid Sequencing

Fractions from the lactose agarose column with high exo-galactanase activity were pooled, concentrated 16-fold using a centricon 10 (Amicon), and separated according to apparent molecular weight on a 12.5% SDS polyacrylamide gel. After electrophoresis, proteins were transferred onto a ProBlott membrane (transfer buffer 10 mM CAPS pH 11 in 10% methanol). The ProBlott membrane was stained in 0.1% Coomassie Brilliant Blue R250 in 1% acetic acid, 40% methanol and destained in 50% methanol. Several protein bands were visible. Two bands, of approximate molecular weight 40 kDa and 80 kDa, in fractions coincident with exo-galactanase activity, were excised and subjected to N-terminal amino acid sequencing on an ABI model 475 protein sequencer.

The 80 kDa tomato polypeptide was identified as an exogalactanase by its homology to the lupin enzyme.

80 kDa Tomato polypeptide: SVSYDDRAI* * NG*R (Seq ID No. 11) Lupin Exo-galactanase: SVTYDHKAIMINGQR . . . etc (SEQ ID No. 3) (*=unassigned amino acid)

The identity of the 40 kDa protein is unknown: 40 kDa Tomato polypeptide: FSNNNFVATDGTHFALNGKS (Seq ID No. 12)

The retention of exo-galactanase activity is highly dependent on ionic strength, and activity can be lost if the ionic strength of chromatography buffers etc. is less than 100 mM. An improved purification procedure would be to include 100 mM NaCl (minimum) in all chromatography buffers. The above protocol would need re-evaluation and optimisation to realise the same purification but yield of exo-galactanase protein and activity should be enhanced.

Isolation of Partial cDNA Clones Encoding Tomato exo-galactanase

Using a heterologous cDNA probe (2628 bp) coding for lupin exo-galactanase and a hybridization temperature of 55° C., 2 partial cDNA clones, TEG13 (1082 bp) and TEG6 (415 bp), were isolated from a commercial tomato fruit (breaker stage) cDNA library obtained from Clontech Laboratories Inc. [prepared using mRNA from ripening (breaker stage) fruit (*Ailsa craig* cultivar VFN8), primed with oligo-(dT) and random primers and cloned into lambda gt11]. Approximately 300,000 cDNA clones from this library were screened using a $^{32}$P-dCTP (Amersham International plc) radiolabelled probe prepared using a kit supplied by United States Biochemicals Inc. (Sequenase v2.0). Unincorporated nucleotides were removed by chromatography through a Sephadex G-50 column. Both clones TEG13 and TEG6 were PCR amplified using TAQ polymerase and lambda gt11 specific primers (GT11 5'B: ACTCCTGGATCCCGT-CAGTAT. Seq ID No. 13; and GT11 3'K: TAATGGTAC-CGACCGGCGCTCT. Seq ID No. 14) cloned into pT7 Blue PCR cloning vector (AMS Biotechnology Limited) and transformed into competent *E. coli*, according to the manufacturer's instructions. Colonies containing recombinant plasmids were used to inoculate 30 ml Lennox Broth containing 100 μg/μl Carbenicillin: after overnight growth at 37° C., plasmid DNA was purified using a Qiagen plasmid DNA extraction kit, PEG precipitated and washed thoroughly with 70% EtOH.

DNA sequence data were obtained using an automated ABI sequencer, and analysed using an Apple Mac computer and DNAstar software. TEG13 exhibited 64.2% homology with nucleotides 678 to 1760 of the lupin exo-galactanase sequence. TEG6 exhibited 62.7% homology with nucleotides 2014 to 2428 of the lupin exo-galactanase sequence.

Isolation of an Overlapping cDNA Fragment

Because the cDNA clones TEG13 and TEG6 aligned with discreet regions of the lupin exo-galactanase cDNA, a RACE procedure was performed (according to Frohman M, Rapid amplification of cDNA ends (RACE): User friendly cDNA cloning, Amplifications: A forum for PCR users, pp 11–14) in order to obtain an overlapping cDNA fragment (5' extension of TEG6). A 5' cDNA pool was prepared by reverse transcription of tomato fruit (breaker stage) total RNA with MuMLV-RT and random hexanucleotide primers, and subsequent tailing with terminal deoxy-transferase (BRL) in the presence of dATP. In a first round PCR amplification of the 5' cDNA pool, the primer 6A1 (position 84-64 in TEG6 and 1844-1824 in FIG. 5) was used in combination with an outer adaptor primer ($R_O$: AAGGATCCGTCGACATC, Seq ID No. 15) and (($dT)_{17}$-$R_i$-$R_O$: AAGGATCCGTCGACATCGATAATACGACTCA CTATAGGGATTTTTTTTTTTTTTTT, Seq ID No. 16) which annealed to the 5' tail of the cDNA. In a second round of PCR amplification, the primer 6A3 (position 42-22 in TEG6 and 1802-1782 in FIG. 5) was used in combination with a nested inner adaptor primer ($R_i$: GACATCGATAATACGAC, Seq. ID No. 17), again annealing to the 5' tail of the cDNA. A RACE product of 511 bp was obtained, extending 469 bp beyond the 5' end of TEG6. This treatment was cloned into pT7 and sequenced. The sequence data revealed that the 5' 209 bp of the RACE product was 100% homologous to the 3' end of TEG13, suggesting that TEG13 and TEG6 were 2 partial cDNA clones representing the same gene (TEG1). A homology of 59.2% was found between this overlapping RACE product (TEG7) and nucleotides 1544–2054 of lupin exo-galactanase.

All DNA alignments were calculated using a DNAStar Megalign program (multiple alignment using the Clustal method. Gap penalty: 10, Gap length penalty: 10).

By overlapping the sequences of TEG13, TEG7 and TEG6, a hybrid cDNA molecule of 1757 bp length, containing a continuous open reading frame, is formed. The encoded polypeptide exhibits 68.1% identity to amino acids 135 to 717 of lupin exo-galactanase.

In order to obtain the sequence information at the 5' end of this clone, 3 subsequent RACE experiments were performed on the 5' tomato cDNA pool (5 µl).

1st 5' RACE

In the first round of PCR amplification, the primer 13A2 (position 106-86 in TEG13 and 524-504 in FIG. 5) was used in combination with the outer adaptor primer ($R_O$) to amplify sequences from the 5' cDNA pool. In the second round of PCR, the primer 13A5 (position 62-42 in TEG13 and 480-460 in FIG. 5) was used in combination with the inner adaptor primer ($R_i$). A specific fragment of 214 bp was recovered from a 0.8% agarose gel using DEAE paper, cloned into plasmid pT7 and transformed into competent *E. coli*. The resultant clone was called 5'TEG1.1 and had a 62 bp overlap with the hybrid cDNA molecule, extending the sequence to 1909 bp.

2nd 5' RACE 2 new primers, 1A1 (position 28-8 in 5'TEG1.1 and 294-274 in FIG. 5) and 1A2 (position 63-43 in 5'TEG1.1 and 329-309 in FIG. 5) were designed for use in a second RACE experiment. Primer 1A2 was used in the first round of amplification of the 5' cDNA pool and primer 1A1 in the second round of amplification, in combination with $R_O$ and $R_i$ respectively. A fragment of 206 bp, was obtained, purified, cloned and sequenced as described above. The clone was called 5'TEG1.2 and had a 26 bp overlap with the extended hybrid cDNA molecule, further extending the sequence to 2089 bp. The 5' end of the extended sequence encoded the C terminal 10 amino acids of a signal peptide followed by the mature N-terminus of tomato exo-galactanase (11/12 amino acids conserved with the N-terminus of purified tomato exogalactanase described above).

3rd 5' RACE

In order to obtain sequence encoding a complete signal peptide, 2 further primers, 1A6 (position 52-32 in 5'TEG1.2 and 138-118 in FIG. 5) and 1A7 (position 32-12 in 5'TEG1.2 and 118-98 in FIG. 5) were synthezised. Primer 1A6 was used in a first round of amplification and primer 1A7 in the second round, as described above. A cDNA product of 117 bp was obtained, purified, cloned and sequenced as above. The clone was called 5'TEG1.3 and had a 32 bp overlap with the extended hybrid cDNA molecule, further extending the sequence to 2175 bp. The extended sequence encoded a complete signal peptide of 25 aa.

3' RACE

In order to obtain a cDNA molecule corresponding to the 3' end of the TEG1 gene, a RACE experiment was carried out on a 3'cDNA pool derived from reverse transcription of tomato fruit (breaker stage) total RNA with MuMLV-RT and the $(dT)_{17}$-$R_i$-$R_O$ primer. The primer 6S2 (position 340-360 in TEG6 and 2100-2120 in FIG. 5) was used in the first PCR reaction, in combination with $R_O$ and the primer 6S3 (position 373-393 in TEG6 and 2133-2153 in FIG. 5) in the second (nested) PCR reaction, in combination with $R_i$. The resultant RACE product was 812 bp long and had a 43 bp overlap with the extended hybrid cDNA molecule, further extending the sequence to 2944 bp, including 23 "A"s ("T"s) at the 3' end.

The complete TEG1 cDNA sequence (Seq ID No. 18) is shown in FIG. 5 and was found to contain a 2514 bp long open reading frame (nucleotide 42 to 2555) encoding a polypeptide (Seq ID No. 19) of 838 amino acids. The signal sequence cleavage site is marked with an arrow. The mature exo-galactanase protein encoded by TEG1 (minus a 25 amino acid signal peptide) is 813 amino acids in length, has a molecular weight of 90.623 daltons and exhibits 70% homology (Lipman-Pearson algorithm, gap penalty: 4. K tuple: 2. length: 12) with the mature exo-galactanase protein encoded by the lupin cDNA and may therefore be regarded as functionally equivalent to the lupin enzyme.

In FIG. 5, nucleotide 1445 is shown as a Y (IUPAC code) whilst in Seq. ID No. 18 in the sequence listing the nucleotide is shown as T. This is purely for convenience: the precise identity of the nucleotide is uncertain. It will be appreciated that, as the nucleotide is at position 3 of a codon, its precise identity is not critical. It will further be noted that the deduced amino acid sequence of the polypeptide encoded by TEG1 differs slightly from the N-terminal sequence of the purified polypeptide as determined by peptide sequencing. Presumably there are a number (at least two) of related genes (e.g. allelic variants) in tomato plants which encode functionally equivalent enzymes having sliohtly different amino acid sequences.

FIG. 6 shows a comparison of the full length amino acid sequences of the lupin enzyme (LEG11CON.pro) and the tomato enzyme (CONTIG.TEG1.PRO). The tomato sequence is shown boxed, and the boxed regions include those portions of the lupin enzyme where the sequence is identical to that of the tomato enzyme. It will be observed that there are several portions of extensive homology (e.g. tomato residues 120–138 & lupin residues 128–146; tomato residues 396–408 & lupin residues 404–416) which may be important to the catalytic function of the molecules.

Construction of Plant Transformation Vectors for Antisense Experiments.

In order to assess the phenotypic consequences of down regulating the expression of TEG1 in transgenic plants, plant transformation vectors were constructed for antisense experiments. The vectors were transferred into *Agrobacterium tumefaciens* LBA4404. Tomato cotyledons (variety "Moneymaker") were infected with *A. tumefaciens* carrying the vectors.

The vector p35S/TEG1A was constructed by inserting a 1082 bp SstI/XbaI fragment of TEG1 (419-1500) in the antisense orientation between the constitutive 35S promoter and the nos ployadenylation signal of pKan35S.

The vector p35S/TEG1B was constructed by inserting a 511 bp SstI/XbaI fragment of TEG1 (1292-1802) in the antisense orientation between the constitutive 35S promoter and the nos ployadenylation site of DKan35S.

The vector pKan35S was constructed by inserting a 0.8 kb HindIII-Xba fragment, containing a 35S cauliflower mosaic virus constitutive promoter (from the vector pcTAK, which vector is described by Toepfer et al., 1987 NAR 15. 5890 et seq.), behind the nos poly-adenylation site of pGPTV-kan (Becker et al., 1992 Plant Molecular Biology 20, 1195–1197).

The vector pPG/TEG1A was constructed by inserting a 1082 bp PstI/Blunt/SstI fragment of TEG1 (419-1500) in the antisense orientation between a fruit-specific (−942 to +33) PG promoter (Bird et al., 1988 Plant Molecular Biology 11, 651–662) and the nos ployadenylation site of pGPTV-kan.

We claim:

1. An isolated nucleic acid encoding an enzyme having exo-(1→4)-β-D-galactanase activity, said enzyme comprising amino acid residues 34–730 of SEQ ID NO:2.

2. An isolated nucleic acid encoding an enzyme having exo-(1→4)-β-D-galactanase activity, said enzyme comprising amino acid residues 26–838 of SEQ ID NO:19.

3. An isolated nucleic acid according to claim 1, comprising a nucleotide sequence selected from the group consisting of nucleotides 163–228, nucleotides 151–228, nucleotides 130–228, and nucleotides 229–2319 of SEQ ID NO:1.

4. An isolated nucleic acid according to claim 2, comprising a nucleotide sequence selected from the group consisting of nucleotides 42–2555 and nucleotides 117–2555, of SEQ ID NO:18.

5. An isolated nucleic acid according to claim 1 or 2, comprising an ATG start signal.

6. An isolated nucleic acid comprising a portion of a nucleotide sequence of SEQ ID NO:1 operably linked in the antisense orientation to a promoter, said sequence being capable of hybridizing with a nucleotide sequence of nucleotides 229–2319 of SEQ ID NO:1.

7. An isolated nucleic acid comprising a portion of a nucleotide sequence of SEQ ID NO:18 operably linked in the antisense orientation to a promoter, said sequence being capable of hybridizing with a nucleotide sequence of nucleotides 117–2555 of SEQ ID NO:18.

8. An isolated nucleic acid sequence according to claim 7, comprising a nucleotide sequence selected from the group consisting of nucleotides 419–1500 and nucleotides 1292–1802, of SEQ ID NO:18 operably linked in the antisense orientation to a promoter.

9. A vector comprising a nucleic acid according to any one of claims 1–4 capable, when introduced into a host cell, of giving rise to an RNA transcript in the host cell.

10. A vector according to claim 9 capable, when introduced into a host cell, of giving rise to a polypeptide having exo-galactanase activity.

11. A host plant or part thereof, into which has been introduced a vector according to any one of claims 6–8, having altered physical characteristics as a result of the introduction.

12. A host cell into which has been introduced a vector according to claim 9.

13. A host plant or part thereof, into which has been introduced a vector according to claim 9, having altered physical characteristics as a result of the introduction.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 2628 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION:130..2319

(xi) SEQUENCE DESCRIPTION: SEQ ID NO: 1:

```
CAACACTCTT ATACAATAAG AGACTCTCAA AAAGTAGCAA AATAAAAAGA CACTATATAC        60

AAAACAGAAA ATATTTCTTC TTCTATAGAA AGACAACATT GCTTATATAG AAACATAGCA       120

TTTTTTGTT ATG TTT GGT TCA AGA ATT GTG ATG GAG AGT TTA ATG TCT          168
          Met Phe Gly Ser Arg Ile Val Met Glu Ser Leu Met Ser
            1               5                  10

AGG AGA AAT TTT CAT ATG GTG TTG CTG TTA TTG TTT TTT TGG GTT TGT        216
Arg Arg Asn Phe His Met Val Leu Leu Leu Leu Phe Phe Trp Val Cys
 15                  20                  25

TAT GTC ACA GCC TCT GTT ACT TAT GAT CAT AAA GCC ATT ATG ATT AAT        264
Tyr Val Thr Ala Ser Val Thr Tyr Asp His Lys Ala Ile Met Ile Asn
 30                  35                  40                  45

GGG CAG AGA AGA ATT TTG ATC TCT GGT TCC ATT CAC TAT CCA AGA AGC        312
Gly Gln Arg Arg Ile Leu Ile Ser Gly Ser Ile His Tyr Pro Arg Ser
                 50                  55                  60

ACA CCT CAG ATG TGG CCA GAC CTT ATT CAA AAG GCC AAA GAT GGA GGG        360
Thr Pro Gln Met Trp Pro Asp Leu Ile Gln Lys Ala Lys Asp Gly Gly
             65                  70                  75

CTT GAT GTT ATA GAG ACT TAT GTG TTC TGG AAT GGA CAT GAA CCT TCT        408
Leu Asp Val Ile Glu Thr Tyr Val Phe Trp Asn Gly His Glu Pro Ser
         80                  85                  90

CCT GGA AAA TAT TAT TTT GAG GAT AGG TTT GAC CTT GTT GGG TTC ATA        456
Pro Gly Lys Tyr Tyr Phe Glu Asp Arg Phe Asp Leu Val Gly Phe Ile
     95                 100                 105

AAG TTG GTT CAG CAA GCT GGT CTA TTT GTT CAT CTC AGG ATT GGT CCT        504
Lys Leu Val Gln Gln Ala Gly Leu Phe Val His Leu Arg Ile Gly Pro
110                 115                 120                 125

TTC ATA TGT GCT GAA TGG AAC TTT GGA GGA TTT CCT GTT TGG CTC AAA        552
Phe Ile Cys Ala Glu Trp Asn Phe Gly Gly Phe Pro Val Trp Leu Lys
                130                 135                 140

TAT GTT CCT GGT ATT GCT TTC AGA ACA GAC AAT GAG CCT TTC AAG GAG        600
Tyr Val Pro Gly Ile Ala Phe Arg Thr Asp Asn Glu Pro Phe Lys Glu
            145                 150                 155

GCA ATG CAA AAA TTC ACT GAG AAG ATT GTA AAT ATA ATG AAA GCA GAG        648
```

```
                Ala Met Gln Lys Phe Thr Glu Lys Ile Val Asn Ile Met Lys Ala Glu
                        160                 165                 170

AAG TTG TTT CAA TCC CAG GGA GGT CCA ATA ATT CTG TCT CAG ATA GAG          696
Lys Leu Phe Gln Ser Gln Gly Gly Pro Ile Ile Leu Ser Gln Ile Glu
        175                 180                 185

AAT GAG TAT GGA CCA GTG GAA TGG GAA ATT GGT GCT CCT GGA AAA GCT          744
Asn Glu Tyr Gly Pro Val Glu Trp Glu Ile Gly Ala Pro Gly Lys Ala
190                 195                 200                 205

TAT ACC AAA TGG GCT GCT CAA ATG GCT GTA GGT CTA GAT ACT GGT GTC          792
Tyr Thr Lys Trp Ala Ala Gln Met Ala Val Gly Leu Asp Thr Gly Val
                210                 215                 220

CCA TGG GTT ATG TGC AAG CAA GAA GAT GCA CTT GAT CCT ATT ATT GAT          840
Pro Trp Val Met Cys Lys Gln Glu Asp Ala Leu Asp Pro Ile Ile Asp
            225                 230                 235

ACC TGC AAT GGA TTT TAC TGT GAA AAC TTC ACT CCA AAC AAG AAC TAC          888
Thr Cys Asn Gly Phe Tyr Cys Glu Asn Phe Thr Pro Asn Lys Asn Tyr
        240                 245                 250

AAA CCC AAA TTG TGG ACA GAA AAT TGG ACT GGC TGG TAC ACT GCT TTT          936
Lys Pro Lys Leu Trp Thr Glu Asn Trp Thr Gly Trp Tyr Thr Ala Phe
255                 260                 265

GGT GGT GCA ACC CCT TAT AGA CCA GCA GAA GAT ATA GCA TTT TCA GTT          984
Gly Gly Ala Thr Pro Tyr Arg Pro Ala Glu Asp Ile Ala Phe Ser Val
270                 275                 280                 285

GCC AGA TTC ATT CAG AAT CGC GGC TCA CTC TTT AAC TAC TAT ATG TAT         1032
Ala Arg Phe Ile Gln Asn Arg Gly Ser Leu Phe Asn Tyr Tyr Met Tyr
                290                 295                 300

CAT GGA GGA ACT AAC TTT GGC CGG ACA TCG AAT GGC CTC TTC GTT GCC         1080
His Gly Gly Thr Asn Phe Gly Arg Thr Ser Asn Gly Leu Phe Val Ala
            305                 310                 315

ACA AGT TAT GAC TAT GAT GCT CCC ATT GAT GAA TAT GGA CTT CTA AAT         1128
Thr Ser Tyr Asp Tyr Asp Ala Pro Ile Asp Glu Tyr Gly Leu Leu Asn
        320                 325                 330

GAA CCA AAA TGG GGG CAT CTG AGA GAA TTA CAT AGA GCA ATA AAA CAA         1176
Glu Pro Lys Trp Gly His Leu Arg Glu Leu His Arg Ala Ile Lys Gln
335                 340                 345

TGC GAG TCG GCT TTA GTG TCG GTG GAT CCC ACA GTG TCA TGG CCT GGA         1224
Cys Glu Ser Ala Leu Val Ser Val Asp Pro Thr Val Ser Trp Pro Gly
350                 355                 360                 365

AAA AAC CTT GAG GTA CAT TTG TAC AAG ACA GAG TCT GCC TGT GCT GCA         1272
Lys Asn Leu Glu Val His Leu Tyr Lys Thr Glu Ser Ala Cys Ala Ala
                370                 375                 380

TTT CTT GCA AAT TAT AAC ACC GAC TAT TCA ACG CAA GTT AAA TTC GGA         1320
Phe Leu Ala Asn Tyr Asn Thr Asp Tyr Ser Thr Gln Val Lys Phe Gly
            385                 390                 395

AAT GGA CAA TAT GAT CTA CCA CCT TGG TCT ATC AGT ATT CTT CCT GAC         1368
Asn Gly Gln Tyr Asp Leu Pro Pro Trp Ser Ile Ser Ile Leu Pro Asp
        400                 405                 410

TGC AAA ACT GAA GTT TTC AAC ACT GCA AAG GTT AAT TCC CCG AGA TTA         1416
Cys Lys Thr Glu Val Phe Asn Thr Ala Lys Val Asn Ser Pro Arg Leu
        415                 420                 425

CAT AGG AAA ATG ACT CCA GTA AAC AGT GCA TTT GCT TGG CAG TCA TAC         1464
His Arg Lys Met Thr Pro Val Asn Ser Ala Phe Ala Trp Gln Ser Tyr
430                 435                 440                 445

AAT GAA GAA CCT GCA TCA TCA AGC GAA AAT GAT CCC GTC ACA GGA TAT         1512
Asn Glu Glu Pro Ala Ser Ser Ser Glu Asn Asp Pro Val Thr Gly Tyr
                450                 455                 460

GCA CTA TGG GAG CAG GTT GGC GTG ACC CGC GAT TCT TCC GAT TAT TTG         1560
Ala Leu Trp Glu Gln Val Gly Val Thr Arg Asp Ser Ser Asp Tyr Leu
            465                 470                 475

TGG TAC CTG ACA GAT GTC AAC ATT GGT CCT AAT GAT ATA AAG GAT GGG         1608
```

```
Trp Tyr Leu Thr Asp Val Asn Ile Gly Pro Asn Asp Ile Lys Asp Gly
        480                 485                 490

AAA TGG CCT GTT CTG ACA GCA ATG TCA GCA GGT CAT GTT CTG AAT GTT      1656
Lys Trp Pro Val Leu Thr Ala Met Ser Ala Gly His Val Leu Asn Val
        495                 500                 505

TTC ATC AAT GGT CAA TAT GCA GGA ACT GCA TAT GGG AGT CTA GAT GAT      1704
Phe Ile Asn Gly Gln Tyr Ala Gly Thr Ala Tyr Gly Ser Leu Asp Asp
510                 515                 520                 525

CCT AGA TTA ACA TTT AGT CAA AGT GTG AAT CTG AGA GTT GGC AAT AAC      1752
Pro Arg Leu Thr Phe Ser Gln Ser Val Asn Leu Arg Val Gly Asn Asn
                530                 535                 540

AAG ATT TCT TTA CTT AGT GTT TCC GTT GGT CTC GCG AAT GTT GGT ACT      1800
Lys Ile Ser Leu Leu Ser Val Ser Val Gly Leu Ala Asn Val Gly Thr
            545                 550                 555

CAC TTT GAG ACA TGG AAT ACT GGA GTG CTT GGT CCA GTC ACA CTG ACA      1848
His Phe Glu Thr Trp Asn Thr Gly Val Leu Gly Pro Val Thr Leu Thr
                560                 565                 570

GGT CTA AGT AGC GGA ACA TGG GAT CTT TCG AAG CAA AAA TGG TCT TAC      1896
Gly Leu Ser Ser Gly Thr Trp Asp Leu Ser Lys Gln Lys Trp Ser Tyr
        575                 580                 585

AAG ATT GGT CTG AAA GGT GAA AGC TTG AGC CTT CAT ACT GAA GCT GGG      1944
Lys Ile Gly Leu Lys Gly Glu Ser Leu Ser Leu His Thr Glu Ala Gly
590                 595                 600                 605

AGT AAC TCT GTT GAA TGG GTA CAA GGA TCT TTA GTG GCT AAA AAA CAA      1992
Ser Asn Ser Val Glu Trp Val Gln Gly Ser Leu Val Ala Lys Lys Gln
                610                 615                 620

CCT TTG GCA TGG TAT AAG ACA ACT TTT AGC GCA CCA GCC GGC AAC GAT      2040
Pro Leu Ala Trp Tyr Lys Thr Thr Phe Ser Ala Pro Ala Gly Asn Asp
            625                 630                 635

CCG TTG GCT CTG GAT TTA GGT AGC ATG GGT AAG GGT GAA GTA TGG GTA      2088
Pro Leu Ala Leu Asp Leu Gly Ser Met Gly Lys Gly Glu Val Trp Val
                640                 645                 650

AAT GGT CAA AGC ATT GGA CGC CAT TGG CCT GGA AAT AAA GCT CGT GGT      2136
Asn Gly Gln Ser Ile Gly Arg His Trp Pro Gly Asn Lys Ala Arg Gly
        655                 660                 665

AAT TGC GGC AAT TGT AAT TAC GCT GGA ACT TAT ACC GAT ACA AAA TGC      2184
Asn Cys Gly Asn Cys Asn Tyr Ala Gly Thr Tyr Thr Asp Thr Lys Cys
670                 675                 680                 685

TTA GCA AAC TGT GGA CAA CCC TCC CAA AGA TGG TAT CAT GTT CCT CGG      2232
Leu Ala Asn Cys Gly Gln Pro Ser Gln Arg Trp Tyr His Val Pro Arg
                690                 695                 700

TCA TGG CTG AGA TCG GGT GGT AAC TAC TTG GTT GTG CTA GAA GAA TGG      2280
Ser Trp Leu Arg Ser Gly Gly Asn Tyr Leu Val Val Leu Glu Glu Trp
            705                 710                 715

GGA GGT GAT CCT AAT GGA ATT GCT TTG GTG GAA AGA ACA TAAAGTGTAT      2329
Gly Gly Asp Pro Asn Gly Ile Ala Leu Val Glu Arg Thr
                720                 725                 730

TCATGTGATA CCAAATGTAC ATGTTATGTA CATAGTGAAA CTATTATGCT GAATATTGTT   2389

CCATATACTA CATTACAGGG TTTGTGTCAC AATGAACATT GAGTCCTTAA ACATTGGTAT   2449

AGAAGGGAAA GAGTTGAATA CCCAAAATGG GTCAAAATAC TACATTGTCC TAGAAATAGA   2509

TTTCTTTCAT TTTCTATATC AACTATTATG TAAGAACAAA TTGAAAGTAA TACTAATAAA   2569

TAGTGATGCA TTTGGATTAA AAAAAAAAAA AAAAAAAAAA AAAAAAAAAA AAAAAAAA    2628

(2) INFORMATION FOR SEQ ID NO: 2:

(i) SEQUENCE CHARACTERISTICS:
        (A) LENGTH: 730 amino acids
        (B) TYPE: amino acid
        (D) TOPOLOGY: linear
```

(ii) MOLECULE TYPE: protein (xi) SEQUENCE DESCRIPTION: SEQ ID NO: 2:

```
Met Phe Gly Ser Arg Ile Val Met Glu Ser Leu Met Ser Arg Arg Asn
 1               5                  10                  15

Phe His Met Val Leu Leu Leu Phe Phe Trp Val Cys Tyr Val Thr
                20                  25                  30

Ala Ser Val Thr Tyr Asp His Lys Ala Ile Met Ile Asn Gly Gln Arg
                35                  40                  45

Arg Ile Leu Ile Ser Gly Ser Ile His Tyr Pro Arg Ser Thr Pro Gln
     50                  55                  60

Met Trp Pro Asp Leu Ile Gln Lys Ala Lys Asp Gly Gly Leu Asp Val
 65                  70                  75                  80

Ile Glu Thr Tyr Val Phe Trp Asn Gly His Glu Pro Ser Pro Gly Lys
                 85                  90                  95

Tyr Tyr Phe Glu Asp Arg Phe Asp Leu Val Gly Phe Ile Lys Leu Val
                100                 105                 110

Gln Gln Ala Gly Leu Phe Val His Leu Arg Ile Gly Pro Phe Ile Cys
            115                 120                 125

Ala Glu Trp Asn Phe Gly Gly Phe Pro Val Trp Leu Lys Tyr Val Pro
130                 135                 140

Gly Ile Ala Phe Arg Thr Asp Asn Glu Pro Phe Lys Glu Ala Met Gln
145                 150                 155                 160

Lys Phe Thr Glu Lys Ile Val Asn Ile Met Lys Ala Glu Lys Leu Phe
                165                 170                 175

Gln Ser Gln Gly Gly Pro Ile Ile Leu Ser Gln Ile Glu Asn Glu Tyr
            180                 185                 190

Gly Pro Val Glu Trp Glu Ile Gly Ala Pro Gly Lys Ala Tyr Thr Lys
            195                 200                 205

Trp Ala Ala Gln Met Ala Val Gly Leu Asp Thr Gly Val Pro Trp Val
        210                 215                 220

Met Cys Lys Gln Glu Asp Ala Leu Asp Pro Ile Ile Asp Thr Cys Asn
225                 230                 235                 240

Gly Phe Tyr Cys Glu Asn Phe Thr Pro Asn Lys Asn Tyr Lys Pro Lys
                245                 250                 255

Leu Trp Thr Glu Asn Trp Thr Gly Trp Tyr Thr Ala Phe Gly Gly Ala
                260                 265                 270

Thr Pro Tyr Arg Pro Ala Glu Asp Ile Ala Phe Ser Val Ala Arg Phe
        275                 280                 285

Ile Gln Asn Arg Gly Ser Leu Phe Asn Tyr Tyr Met Tyr His Gly Gly
    290                 295                 300

Thr Asn Phe Gly Arg Thr Ser Asn Gly Leu Phe Val Ala Thr Ser Tyr
305                 310                 315                 320

Asp Tyr Asp Ala Pro Ile Asp Glu Tyr Gly Leu Leu Asn Glu Pro Lys
                325                 330                 335

Trp Gly His Leu Arg Glu Leu His Arg Ala Ile Lys Gln Cys Glu Ser
            340                 345                 350

Ala Leu Val Ser Val Asp Pro Thr Val Ser Trp Pro Gly Lys Asn Leu
            355                 360                 365

Glu Val His Leu Tyr Lys Thr Glu Ser Ala Cys Ala Ala Phe Leu Ala
        370                 375                 380

Asn Tyr Asn Thr Asp Tyr Ser Thr Gln Val Lys Phe Gly Asn Gly Gln
385                 390                 395                 400
```

-continued

```
Tyr Asp Leu Pro Pro Trp Ser Ile Ser Ile Leu Pro Asp Cys Lys Thr
            405                 410                 415

Glu Val Phe Asn Thr Ala Lys Val Asn Ser Pro Arg Leu His Arg Lys
            420                 425                 430

Met Thr Pro Val Asn Ser Ala Phe Ala Trp Gln Ser Tyr Asn Glu Glu
            435                 440                 445

Pro Ala Ser Ser Ser Glu Asn Asp Pro Val Thr Gly Tyr Ala Leu Trp
            450                 455                 460

Glu Gln Val Gly Val Thr Arg Asp Ser Ser Asp Tyr Leu Trp Tyr Leu
465                 470                 475                 480

Thr Asp Val Asn Ile Gly Pro Asn Asp Ile Lys Asp Gly Lys Trp Pro
                    485                 490                 495

Val Leu Thr Ala Met Ser Ala Gly His Val Leu Asn Val Phe Ile Asn
                    500                 505                 510

Gly Gln Tyr Ala Gly Thr Ala Tyr Gly Ser Leu Asp Asp Pro Arg Leu
                    515                 520                 525

Thr Phe Ser Gln Ser Val Asn Leu Arg Val Gly Asn Asn Lys Ile Ser
                    530                 535                 540

Leu Leu Ser Val Ser Val Gly Leu Ala Asn Val Gly Thr His Phe Glu
545                 550                 555                 560

Thr Trp Asn Thr Gly Val Leu Gly Pro Val Thr Leu Thr Gly Leu Ser
                    565                 570                 575

Ser Gly Thr Trp Asp Leu Ser Lys Gln Lys Trp Ser Tyr Lys Ile Gly
                    580                 585                 590

Leu Lys Gly Glu Ser Leu Ser Leu His Thr Glu Ala Gly Ser Asn Ser
                    595                 600                 605

Val Glu Trp Val Gln Gly Ser Leu Val Ala Lys Lys Gln Pro Leu Ala
            610                 615                 620

Trp Tyr Lys Thr Thr Phe Ser Ala Pro Ala Gly Asn Asp Pro Leu Ala
625                 630                 635                 640

Leu Asp Leu Gly Ser Met Gly Lys Gly Glu Val Trp Val Asn Gly Gln
                    645                 650                 655

Ser Ile Gly Arg His Trp Pro Gly Asn Lys Ala Arg Gly Asn Cys Gly
                    660                 665                 670

Asn Cys Asn Tyr Ala Gly Thr Tyr Thr Asp Thr Lys Cys Leu Ala Asn
                    675                 680                 685

Cys Gly Gln Pro Ser Gln Arg Trp Tyr His Val Pro Arg Ser Trp Leu
            690                 695                 700

Arg Ser Gly Gly Asn Tyr Leu Val Val Leu Glu Glu Trp Gly Gly Asp
705                 710                 715                 720

Pro Asn Gly Ile Ala Leu Val Glu Arg Thr
                    725                 730
```

(2) INFORMATION FOR SEQ ID NO: 3:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 3:

Ser Val Thr Tyr Asp His Lys Ala Ile Met Ile Asn Gly Gln Arg Arg
1               5                   10                  15

Leu Ile Ser (2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 4:

Ser Val Thr Tyr Asp His Lys Ala Ile Met Ile Asn
1               5                   10

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 5:

Val Ala Lys Lys Gln Pro Leu Ala Trp Tyr
1               5                   10

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 6:

ATCATDATNG CYTTRTGRTC RTA                                              23

(2) INFORMATION FOR SEQ ID NO: 7:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 7:

Val Ala Lys Lys Gln Pro Leu Ala Trp Tyr Lys Thr Thr
1               5                   10

(2) INFORMATION FOR SEQ ID NO: 8:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 8:

Phe Ser Ala Pro Ala Gly Asn Asp Pro Leu
1               5                   10

(2) INFORMATION FOR SEQ ID NO: 9:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 9:

Gly Glu Val Trp Val Asn Gly Gln Ser Ile Gly
1               5                   10

(2) INFORMATION FOR SEQ ID NO: 10:

(i) SEQUENCE CHARACTERISTICS:
         (A) LENGTH: 16 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 10:

Gly Asn Cys Gly Asn Cys Asn Tyr Ala Gly Thr Tyr Thr Asp Thr Lys
1               5                   10                  15

(2) INFORMATION FOR SEQ ID NO: 11:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 11:

Ser Val Ser Tyr Asp Asp Arg Ala Ile
1               5

(2) INFORMATION FOR SEQ ID NO: 12:

(i) SEQUENCE CHARACTERISTICS:
             (A) LENGTH: 20 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 12:

Phe Ser Asn Asn Asn Phe Val Ala Thr Asp Gly Thr His Phe Ala Leu
1               5                   10                  15

Asn Gly Lys Ser
            20

(2) INFORMATION FOR SEQ ID NO: 13:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION:  /desc = "synthetic oligonucleotide"

(iii) HYPOTHETICAL: NO (iv) ANTI-SENSE: NO (xi) SEQUENCE DESCRIPTION: SEQ ID NO: 13:

ACTCCTGGAT CCCGTCAGTA T                                                         21

(2) INFORMATION FOR SEQ ID NO: 14:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION:  /desc = "synthetic oligonucleotide"

(iii) HYPOTHETICAL: NO (iv) ANTI-SENSE: NO (xi) SEQUENCE DESCRIPTION: SEQ ID NO: 14:

TAATGGTACC GACCGGCGCT CT                                                        22

(2) INFORMATION FOR SEQ ID NO: 15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: NO (iv) ANTI-SENSE: NO (xi) SEQUENCE DESCRIPTION: SEQ ID NO: 15:

AAGGATCCGT CGACATC                                            17

(2) INFORMATION FOR SEQ ID NO: 16:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: NO (iv) ANTI-SENSE: NO (xi) SEQUENCE DESCRIPTION: SEQ ID NO: 16:

AAGGATCCGT CGACATCGAT AATACGACTC ACTATAGGGA TTTTTTTTTT TTTTTTT      57

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: NO (iv) ANTI-SENSE: NO (xi) SEQUENCE DESCRIPTION: SEQ ID NO: 17:

GACATCGATA ATACGAC                                            17

(2) INFORMATION FOR SEQ ID NO: 18:

(i) SEQUENCE CHARACTERISTICS:
        (A) LENGTH: 2944 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION:42..2555

(xi) SEQUENCE DESCRIPTION: SEQ ID NO: 18:

```
TTAAAAAGGC ACAATCTTGA TAGAAAAGGA GATAATTTTA C ATG GGT TGT ACG        53
                                              Met Gly Cys Thr

CTT ATA CTA ATG TTG AAT GTG TTG TTG GTG TTG TTG GGT TCA TGG GTT     101
Leu Ile Leu Met Leu Asn Val Leu Leu Val Leu Leu Gly Ser Trp Val
735             740             745             750

TTT TCT GGA ACA GCT TCT GTT TCA TAT GAC CAT AGG GCT ATT ATT GTA     149
Phe Ser Gly Thr Ala Ser Val Ser Tyr Asp His Arg Ala Ile Ile Val
                755             760             765

AAT GGA CAA AGA AGA ATA CTT ATT TCT GGT TCT GTT CAT TAT CCA AGA     197
Asn Gly Gln Arg Arg Ile Leu Ile Ser Gly Ser Val His Tyr Pro Arg
            770             775             780

AGC ACT CCT GAG ATG TGG CCA GGT ATT ATT CAA AAG GCT AAA GAA GGA     245
Ser Thr Pro Glu Met Trp Pro Gly Ile Ile Gln Lys Ala Lys Glu Gly
        785             790             795

GGT GTG GAT GTG ATT CAG ACT TAT GTT TTC TGG AAT GGA CAT GAG CCT     293
Gly Val Asp Val Ile Gln Thr Tyr Val Phe Trp Asn Gly His Glu Pro
    800             805             810

CAA CAA GGG AAA TAT TAT TTT GAA GGG AGA TAT GAT TTA GTG AAG TTT     341
Gln Gln Gly Lys Tyr Tyr Phe Glu Gly Arg Tyr Asp Leu Val Lys Phe
815             820             825             830

ATT AAG CTG GTG CAC CAA GCA GGA CTT TAT GTC CAT CTT AGA GTT GGA     389
Ile Lys Leu Val His Gln Ala Gly Leu Tyr Val His Leu Arg Val Gly
                835             840             845

CCT TAT GCT TGT GCT GAA TGG AAT TTT GGG GGC TTT CCT GTT TGG CTG     437
Pro Tyr Ala Cys Ala Glu Trp Asn Phe Gly Gly Phe Pro Val Trp Leu
            850             855             860

AAA TAT GTT CCA GGT ATC AGT TTC AGA ACA GAT AAT GGA CCT TTC AAG     485
Lys Tyr Val Pro Gly Ile Ser Phe Arg Thr Asp Asn Gly Pro Phe Lys
        865             870             875

GCT GCA ATG CAA AAA TTT ACT GCC AAG ATT GTC AAT ATG ATG AAA GCG     533
Ala Ala Met Gln Lys Phe Thr Ala Lys Ile Val Asn Met Met Lys Ala
    880             885             890

GAA CGT TTG TAT GAA ACT CAA GGG GGG CCA ATA ATT TTA TCT CAG ATT     581
Glu Arg Leu Tyr Glu Thr Gln Gly Gly Pro Ile Ile Leu Ser Gln Ile
895             900             905             910

GAG AAT GAA TAT GGA CCC ATG GAA TGG GAA CTG GGA GCA CCA GGT AAA     629
Glu Asn Glu Tyr Gly Pro Met Glu Trp Glu Leu Gly Ala Pro Gly Lys
                915             920             925

TCT TAC GCA CAG TGG GCC GCC AAA ATG GCT GTG GGT CTT GAC ACT GGT     677
Ser Tyr Ala Gln Trp Ala Ala Lys Met Ala Val Gly Leu Asp Thr Gly
            930             935             940

GTC CCA TGG GTT ATG TGC AAG CAA GAC GAT GCC CCT GAT CCT ATT ATA     725
Val Pro Trp Val Met Cys Lys Gln Asp Asp Ala Pro Asp Pro Ile Ile
        945             950             955

AAT GCT TGC AAT GGC TTC TAC TGT GAC TAC TTT TCT CCA AAC AAG GCT     773
Asn Ala Cys Asn Gly Phe Tyr Cys Asp Tyr Phe Ser Pro Asn Lys Ala
    960             965             970

TAT AAA CCA AAG ATA TGG ACT GAA GCC TGG ACT GCA TGG TTT ACT GGT     821
Tyr Lys Pro Lys Ile Trp Thr Glu Ala Trp Thr Ala Trp Phe Thr Gly
975             980             985             990

TTT GGA AAT CCA GTT CCT TAC CGT CCT GCT GAG GAC TTG GCA TTT TCT     869
Phe Gly Asn Pro Val Pro Tyr Arg Pro Ala Glu Asp Leu Ala Phe Ser
                995             1000            1005

GTT GCA AAA TTT ATA CAG AAG GGA GGT TCC TTC ATC AAT TAT TAC ATG     917
Val Ala Lys Phe Ile Gln Lys Gly Gly Ser Phe Ile Asn Tyr Tyr Met
            1010            1015            1020

TAT CAT GGA GGA ACA AAC TTT GGA CGG ACT GCT GGT GGT CCA TTT ATT     965
Tyr His Gly Gly Thr Asn Phe Gly Arg Thr Ala Gly Gly Pro Phe Ile
        1025            1030            1035

GCT ACT AGT TAT GAC TAT GAT GCA CCA CTT GAT GAA TAT GGA TTA TTG    1013
```

```
Ala Thr Ser Tyr Asp Tyr Asp Ala Pro Leu Asp Glu Tyr Gly Leu Leu
    1040            1045                1050

CGA CAA CCA AAA TGG GGT CAC CTG AAA GAT CTG CAT AGA GCA ATA AAG      1061
Arg Gln Pro Lys Trp Gly His Leu Lys Asp Leu His Arg Ala Ile Lys
1055            1060                1065                1070

CTT TGT GAA CCA GCT TTA GTC TCT GGA GAT CCA GCT GTG ACA GCA CTT      1109
Leu Cys Glu Pro Ala Leu Val Ser Gly Asp Pro Ala Val Thr Ala Leu
                1075                1080                1085

GGA CAC CAG CAG GAG GCC CAT GTT TTT AGG TCG AAG GCT GGC TCT TGT      1157
Gly His Gln Gln Glu Ala His Val Phe Arg Ser Lys Ala Gly Ser Cys
            1090                1095                1100

GCT GCA TTC CTT GCT AAC TAC GAC CAA CAC TCT TTT GCT ACT GTG TCA      1205
Ala Ala Phe Leu Ala Asn Tyr Asp Gln His Ser Phe Ala Thr Val Ser
        1105                1110                1115

TTT GCA AAC AGG CAT TAC AAC TTG CCA CCA TGG TCA ATC AGC ATT CTT      1253
Phe Ala Asn Arg His Tyr Asn Leu Pro Pro Trp Ser Ile Ser Ile Leu
    1120                1125                1130

CCC GAC TGC AAG AAC ACT GTA TTT AAT ACA GCA CGG ATC GGT GCT CAA      1301
Pro Asp Cys Lys Asn Thr Val Phe Asn Thr Ala Arg Ile Gly Ala Gln
1135            1140                1145                1150

AGT GCT CAG ATG AAG ATG ACT CCA GTC AGC AGA GGA TTG CCC TGG CAG      1349
Ser Ala Gln Met Lys Met Thr Pro Val Ser Arg Gly Leu Pro Trp Gln
                1155                1160                1165

TCA TTC AAT GAA GAG ACA TCA TCT TAT GAA GAC AGT AGT TTT ACA GTT      1397
Ser Phe Asn Glu Glu Thr Ser Ser Tyr Glu Asp Ser Ser Phe Thr Val
            1170                1175                1180

GTT GGG CTA TTG GAA CAG ATA AAT ACA ACA AGA GAC GTG TCT GAT TAT      1445
Val Gly Leu Leu Glu Gln Ile Asn Thr Thr Arg Asp Val Ser Asp Tyr
        1185                1190                1195

TTG TGG TAT TCA ACA GAT GTC AAG ATT GAT TCA AGA GAA AAG TTT TTG      1493
Leu Trp Tyr Ser Thr Asp Val Lys Ile Asp Ser Arg Glu Lys Phe Leu
    1200                1205                1210

AGA GGC GGA AAA TGG CCT TGG CTT ACG ATC ATG TCA GCT GGG CAT GCA      1541
Arg Gly Gly Lys Trp Pro Trp Leu Thr Ile Met Ser Ala Gly His Ala
1215            1220                1225                1230

TTG CAT GTT TTT GTG AAT GGT CAA TTA GCA GGA ACT GCA TAT GGA AGT      1589
Leu His Val Phe Val Asn Gly Gln Leu Ala Gly Thr Ala Tyr Gly Ser
                1235                1240                1245

TTA GAA AAA CCG AAA CTA ACT TTC AGT AAA GCC GTA AAT CTG AGA GCA      1637
Leu Glu Lys Pro Lys Leu Thr Phe Ser Lys Ala Val Asn Leu Arg Ala
            1250                1255                1260

GGT GTT AAC AAG ATT TCT CTA CTG AGC ATT GCT GTT GGC CTT CCG AAT      1685
Gly Val Asn Lys Ile Ser Leu Leu Ser Ile Ala Val Gly Leu Pro Asn
        1265                1270                1275

ATC GGC CCA CAT TTT GAG ACA TGG AAT GCT GGT GTT CTT GGG CCA GTC      1733
Ile Gly Pro His Phe Glu Thr Trp Asn Ala Gly Val Leu Gly Pro Val
    1280                1285                1290

TCA CTA ACT GGT CTT GAC GAG GGG AAA AGA GAT TTA ACA TGG CAG AAA      1781
Ser Leu Thr Gly Leu Asp Glu Gly Lys Arg Asp Leu Thr Trp Gln Lys
1295            1300                1305                1310

TGG TTC TAC AAG GTT GGT CTA AAA GGA GAA GCC CTG AGT CTT CAT TCA      1829
Trp Phe Tyr Lys Val Gly Leu Lys Gly Glu Ala Leu Ser Leu His Ser
                1315                1320                1325

CTC AGT GGT AGC CCA TCC GTG GAG TGG GTG GAA GGC TCT TTA GTG GCA      1877
Leu Ser Gly Ser Pro Ser Val Glu Trp Val Glu Gly Ser Leu Val Ala
            1330                1335                1340

CAG AAG CAG CCA CTC AGT TGG TAT AAG ACT ACA TTC AAT GCT CCA GAT      1925
Gln Lys Gln Pro Leu Ser Trp Tyr Lys Thr Thr Phe Asn Ala Pro Asp
        1345                1350                1355

GGA AAT GAA CCT TTG GCT TTA GAT ATG AAT ACC ATG GGC AAA GGT CAA      1973
```

```
Gly Asn Glu Pro Leu Ala Leu Asp Met Asn Thr Met Gly Lys Gly Gln
    1360                1365                1370

GTA TGG ATA AAT GGT CAG AGC CTC GGA CGC CAC TGG CCT GCA TAT AAA         2021
Val Trp Ile Asn Gly Gln Ser Leu Gly Arg His Trp Pro Ala Tyr Lys
1375                1380                1385                1390

TCA TCT GGA AGT TGT AGT GTC TGT AAC TAT ACT GGC TGG TTT GAT GAG         2069
Ser Ser Gly Ser Cys Ser Val Cys Asn Tyr Thr Gly Trp Phe Asp Glu
                1395                1400                1405

AAA AAG TGC CTA ACT AAC TGT GGT GAG GGC TCA CAA AGA TGG TAC CAC         2117
Lys Lys Cys Leu Thr Asn Cys Gly Glu Gly Ser Gln Arg Trp Tyr His
            1410                1415                1420

GTA CCC CGG TCT TGG CTG TAT CCT ACT GGA AAT TTG TTA GTT GTA TTC         2165
Val Pro Arg Ser Trp Leu Tyr Pro Thr Gly Asn Leu Leu Val Val Phe
        1425                1430                1435

GAG GAA TGG GGA GGA GAT CCT TAT GGA ATC ACT TTA GTC AAA AGA GAA         2213
Glu Glu Trp Gly Gly Asp Pro Tyr Gly Ile Thr Leu Val Lys Arg Glu
    1440                1445                1450

ATA GGG AGT GTT TGT GCT GAT ATA TAT GAG TGG CAA CCA CAG TTA TTG         2261
Ile Gly Ser Val Cys Ala Asp Ile Tyr Glu Trp Gln Pro Gln Leu Leu
1455                1460                1465                1470

AAT TGG CAG AGG CTA GTA TCT GGT AAG TTT GAC AGA CCT CTC AGA CCT         2309
Asn Trp Gln Arg Leu Val Ser Gly Lys Phe Asp Arg Pro Leu Arg Pro
                1475                1480                1485

AAA GCC CAT CTT AAG TGT GCA CCT GGT CAG AAG ATT TCT TCA ATC AAA         2357
Lys Ala His Leu Lys Cys Ala Pro Gly Gln Lys Ile Ser Ser Ile Lys
            1490                1495                1500

TTT GCA AGC TTT GGA ACA CCA GAG GGA GTT TGT GGG AAC TTC CAG CAG         2405
Phe Ala Ser Phe Gly Thr Pro Glu Gly Val Cys Gly Asn Phe Gln Gln
        1505                1510                1515

GGA AGC TGC CAT GCT CCG CGC TCA TAT GAT GCT TTC AAA AAG AAT TGT         2453
Gly Ser Cys His Ala Pro Arg Ser Tyr Asp Ala Phe Lys Lys Asn Cys
    1520                1525                1530

GTT GGG AAA GAG TCT TGC TCA GTA CAG GTA ACA CCA GAG AAT TTT GGA         2501
Val Gly Lys Glu Ser Cys Ser Val Gln Val Thr Pro Glu Asn Phe Gly
1535                1540                1545                1550

GGT GAT CCA TGT CGA AAC GTT CTA AAG AAA CTC TCA GTG GAA GCC ATT         2549
Gly Asp Pro Cys Arg Asn Val Leu Lys Lys Leu Ser Val Glu Ala Ile
                1555                1560                1565

TGT AGT TGATAATTCT GAGTATACAA GTGAAAAAAT ACTTGAACCA CTCATATAAA          2605
Cys Ser

CATTTTTCAA ACGAGCTACT AGACATCCAT TAACCCACAC TACCATTTTT TGGCTTTGCT       2665

GGGGTTGAAG TTGTACAGTT AAGCAACACA CCTCTTTGAT CAAAGCTCAC CTGATTATGA       2725

AGATGATTGA CGAAAGATTC TGTACATGTA AGGTTTCGTC TAATTACACA TACAGATATG       2785

ATTCTTGATG AATCGATGTG CAAATTTTGT TTGTGTTAGG GTGAGAGAGA CTTGAAAAGC       2845

ATTTTGCTTT CATGATGTTC TACATTATAC AATCATAATG TAAGTAAGCA AGCAATAATT      2905

CATTGCTTTG CACATTGAAA AAAAAAAAAA AAAAAAAA                              2944
```

(2) INFORMATION FOR SEQ ID NO: 19:

(i) SEQUENCE CHARACTERISTICS:
        (A) LENGTH: 838 amino acids
        (B) TYPE: amino acid
        (D) TOPOLOGY: linear (ii) MOLECULE TYPE: protein (xi) SEQUENCE DESCRIPTION: SEQ ID NO: 19:

```
Met Gly Cys Thr Leu Ile Leu Met Leu Asn Val Leu Val Leu Leu
1               5                   10                  15
```

```
Gly Ser Trp Val Phe Ser Gly Thr Ala Ser Val Ser Tyr Asp His Arg
             20                  25                  30

Ala Ile Ile Val Asn Gly Gln Arg Arg Ile Leu Ile Ser Gly Ser Val
             35                  40                  45

His Tyr Pro Arg Ser Thr Pro Glu Met Trp Pro Gly Ile Ile Gln Lys
         50                  55                  60

Ala Lys Glu Gly Gly Val Asp Val Ile Gln Thr Tyr Val Phe Trp Asn
 65                  70                  75                  80

Gly His Glu Pro Gln Gln Gly Lys Tyr Tyr Phe Glu Gly Arg Tyr Asp
                 85                  90                  95

Leu Val Lys Phe Ile Lys Leu Val His Gln Ala Gly Leu Tyr Val His
             100                 105                 110

Leu Arg Val Gly Pro Tyr Ala Cys Ala Glu Trp Asn Phe Gly Gly Phe
         115                 120                 125

Pro Val Trp Leu Lys Tyr Val Pro Gly Ile Ser Phe Arg Thr Asp Asn
         130                 135                 140

Gly Pro Phe Lys Ala Ala Met Gln Lys Phe Thr Ala Lys Ile Val Asn
145                 150                 155                 160

Met Met Lys Ala Glu Arg Leu Tyr Glu Thr Gln Gly Gly Pro Ile Ile
                 165                 170                 175

Leu Ser Gln Ile Glu Asn Glu Tyr Gly Pro Met Glu Trp Glu Leu Gly
             180                 185                 190

Ala Pro Gly Lys Ser Tyr Ala Gln Trp Ala Ala Lys Met Ala Val Gly
         195                 200                 205

Leu Asp Thr Gly Val Pro Trp Val Met Cys Lys Gln Asp Asp Ala Pro
         210                 215                 220

Asp Pro Ile Ile Asn Ala Cys Asn Gly Phe Tyr Cys Asp Tyr Phe Ser
225                 230                 235                 240

Pro Asn Lys Ala Tyr Lys Pro Lys Ile Trp Thr Glu Ala Trp Thr Ala
                 245                 250                 255

Trp Phe Thr Gly Phe Gly Asn Pro Val Pro Tyr Arg Pro Ala Glu Asp
             260                 265                 270

Leu Ala Phe Ser Val Ala Lys Phe Ile Gln Lys Gly Gly Ser Phe Ile
         275                 280                 285

Asn Tyr Tyr Met Tyr His Gly Gly Thr Asn Phe Gly Arg Thr Ala Gly
         290                 295                 300

Gly Pro Phe Ile Ala Thr Ser Tyr Asp Tyr Asp Ala Pro Leu Asp Glu
305                 310                 315                 320

Tyr Gly Leu Leu Arg Gln Pro Lys Trp Gly His Leu Lys Asp Leu His
                 325                 330                 335

Arg Ala Ile Lys Leu Cys Glu Pro Ala Leu Val Ser Gly Asp Pro Ala
             340                 345                 350

Val Thr Ala Leu Gly His Gln Gln Glu Ala His Val Phe Arg Ser Lys
         355                 360                 365

Ala Gly Ser Cys Ala Ala Phe Leu Ala Asn Tyr Asp Gln His Ser Phe
         370                 375                 380

Ala Thr Val Ser Phe Ala Asn Arg His Tyr Asn Leu Pro Pro Trp Ser
385                 390                 395                 400

Ile Ser Ile Leu Pro Asp Cys Lys Asn Thr Val Phe Asn Thr Ala Arg
                 405                 410                 415

Ile Gly Ala Gln Ser Ala Gln Met Lys Met Thr Pro Val Ser Arg Gly
             420                 425                 430

Leu Pro Trp Gln Ser Phe Asn Glu Glu Thr Ser Ser Tyr Glu Asp Ser
```

-continued

```
                435                 440                 445
Ser Phe Thr Val Val Gly Leu Leu Glu Gln Ile Asn Thr Thr Arg Asp
    450                 455                 460
Val Ser Asp Tyr Leu Trp Tyr Ser Thr Asp Val Lys Ile Asp Ser Arg
465                 470                 475                 480
Glu Lys Phe Leu Arg Gly Gly Lys Trp Pro Trp Leu Thr Ile Met Ser
                485                 490                 495
Ala Gly His Ala Leu His Val Phe Val Asn Gly Gln Leu Ala Gly Thr
                500                 505                 510
Ala Tyr Gly Ser Leu Glu Lys Pro Lys Leu Thr Phe Ser Lys Ala Val
            515                 520                 525
Asn Leu Arg Ala Gly Val Asn Lys Ile Ser Leu Leu Ser Ile Ala Val
            530                 535                 540
Gly Leu Pro Asn Ile Gly Pro His Phe Glu Thr Trp Asn Ala Gly Val
545                 550                 555                 560
Leu Gly Pro Val Ser Leu Thr Gly Leu Asp Glu Gly Lys Arg Asp Leu
                565                 570                 575
Thr Trp Gln Lys Trp Phe Tyr Lys Val Gly Leu Lys Gly Glu Ala Leu
            580                 585                 590
Ser Leu His Ser Leu Ser Gly Ser Pro Ser Val Glu Trp Val Glu Gly
            595                 600                 605
Ser Leu Val Ala Gln Lys Gln Pro Leu Ser Trp Tyr Lys Thr Thr Phe
610                 615                 620
Asn Ala Pro Asp Gly Asn Glu Pro Leu Ala Leu Asp Met Asn Thr Met
625                 630                 635                 640
Gly Lys Gly Gln Val Trp Ile Asn Gly Gln Ser Leu Gly Arg His Trp
                645                 650                 655
Pro Ala Tyr Lys Ser Ser Gly Ser Cys Ser Val Cys Asn Tyr Thr Gly
                660                 665                 670
Trp Phe Asp Glu Lys Lys Cys Leu Thr Asn Cys Gly Glu Gly Ser Gln
            675                 680                 685
Arg Trp Tyr His Val Pro Arg Ser Trp Leu Tyr Pro Thr Gly Asn Leu
            690                 695                 700
Leu Val Val Phe Glu Glu Trp Gly Gly Asp Pro Tyr Gly Ile Thr Leu
705                 710                 715                 720
Val Lys Arg Glu Ile Gly Ser Val Cys Ala Asp Ile Tyr Glu Trp Gln
                725                 730                 735
Pro Gln Leu Leu Asn Trp Gln Arg Leu Val Ser Gly Lys Phe Asp Arg
                740                 745                 750
Pro Leu Arg Pro Lys Ala His Leu Lys Cys Ala Pro Gly Gln Lys Ile
            755                 760                 765
Ser Ser Ile Lys Phe Ala Ser Phe Gly Thr Pro Glu Gly Val Cys Gly
770                 775                 780
Asn Phe Gln Gln Gly Ser Cys His Ala Pro Arg Ser Tyr Asp Ala Phe
785                 790                 795                 800
Lys Lys Asn Cys Val Gly Lys Glu Ser Cys Ser Val Gln Val Thr Pro
                805                 810                 815
Glu Asn Phe Gly Gly Asp Pro Cys Arg Asn Val Leu Lys Lys Leu Ser
                820                 825                 830
Val Glu Ala Ile Cys Ser
            835
```

(2) INFORMATION FOR SEQ ID NO: 20:

```
    (i) SEQUENCE CHARACTERISTICS:
        (A) LENGTH: 731 amino acids
        (B) TYPE: amino acid
        (D) TOPOLOGY: linear (ii) MOLECULE TYPE: protein (xi) SEQUENCE DESCRIPTION: SEQ ID NO: 20:

Met Leu Cys Gly Lys Glu Asn Asn Val Met Lys Met Met Leu Val Tyr
 1               5                  10                  15

Val Phe Val Leu Ile Thr Leu Ile Ser Cys Val Tyr Gly Asn Val Trp
                20                  25                  30

Tyr Asp Tyr Arg Ala Ile Lys Ile Asn Asp Gln Arg Arg Ile Leu Leu
            35                  40                  45

Ser Gly Ser Ile His Tyr Pro Arg Ser Thr Pro Glu Met Trp Pro Asp
 50                  55                  60

Ile Ile Glu Lys Ala Lys Asp Ser Gln Leu Asp Val Ile Gln Thr Tyr
 65                  70                  75                  80

Val Phe Trp Asn Gly His Glu Pro Ser Glu Gly Lys Tyr Tyr Phe Glu
                85                  90                  95

Gly Arg Tyr Asp Leu Val Lys Phe Ile Lys Leu Ile His Gln Ala Gly
            100                 105                 110

Leu Phe Val His Leu Arg Ile Gly Pro Phe Ala Cys Ala Glu Trp Asn
            115                 120                 125

Phe Gly Gly Phe Pro Val Trp Leu Lys Tyr Val Pro Gly Ile Glu Phe
130                 135                 140

Arg Thr Asp Asn Gly Pro Phe Lys Glu Lys Met Gln Val Phe Thr Thr
145                 150                 155                 160

Lys Ile Val Asp Met Met Lys Ala Glu Lys Leu Phe His Trp Gln Gly
                165                 170                 175

Gly Pro Ile Ile Leu Asn Gln Ile Glu Asn Glu Tyr Gly Pro Val Glu
            180                 185                 190

Trp Glu Ile Gly Ala Pro Gly Lys Ala Tyr Thr His Trp Ala Ala Gln
            195                 200                 205

Met Ala Gln Ser Leu Asn Ala Gly Val Pro Trp Ile Met Cys Lys Gln
210                 215                 220

Asp Ser Asp Val Pro Asp Asn Val Ile Asp Thr Cys Asn Gly Phe Tyr
225                 230                 235                 240

Cys Glu Gly Phe Val Pro Lys Asp Lys Ser Lys Pro Lys Met Trp Thr
                245                 250                 255

Glu Asn Trp Thr Gly Trp Tyr Thr Glu Tyr Gly Lys Pro Val Pro Tyr
            260                 265                 270

Arg Pro Ala Glu Asp Val Ala Phe Ser Val Ala Arg Phe Ile Gln Asn
275                 280                 285

Gly Gly Ser Phe Met Asn Tyr Tyr Met Phe His Gly Gly Thr Asn Phe
290                 295                 300

Glu Thr Thr Ala Gly Arg Phe Val Ser Thr Ser Tyr Asp Tyr Asp Ala
305                 310                 315                 320

Pro Leu Asp Glu Tyr Gly Leu Pro Arg Glu Pro Lys Tyr Thr His Leu
                325                 330                 335

Lys Asn Leu His Lys Ala Ile Lys Met Cys Glu Pro Ala Leu Val Ser
            340                 345                 350

Ser Asp Ala Lys Val Thr Asn Leu Gly Ser Asn Gln Glu Ala His Val
355                 360                 365

Tyr Ser Ser Asn Ser Gly Ser Cys Ala Ala Phe Leu Ala Asn Tyr Asp
370                 375                 380
```

```
Pro Lys Trp Ser Val Lys Val Thr Phe Ser Gly Met Glu Phe Glu Leu
385                 390                 395                 400

Pro Ala Trp Ser Ile Ser Ile Leu Pro Asp Cys Lys Lys Glu Val Tyr
                405                 410                 415

Asn Thr Ala Arg Val Asn Glu Pro Ser Pro Lys Leu His Ser Lys Met
            420                 425                 430

Thr Pro Val Ile Ser Asn Leu Asn Trp Gln Ser Tyr Ser Asp Glu Val
        435                 440                 445

Pro Thr Ala Asp Ser Pro Gly Thr Phe Arg Glu Lys Lys Leu Tyr Glu
    450                 455                 460

Gln Ile Asn Met Thr Trp Asp Lys Ser Asp Tyr Leu Trp Tyr Met Thr
465                 470                 475                 480

Asp Val Leu Asp Gly Asn Glu Gly Phe Leu Lys Lys Gly Asp Glu
                485                 490                 495

Pro Trp Leu Thr Val Asn Ser Ala Gly His Val Leu His Val Phe Val
            500                 505                 510

Asn Gly Gln Leu Gln Gly His Ala Tyr Gly Ser Leu Ala Lys Pro Gln
            515                 520                 525

Leu Thr Phe Ser Gln Lys Val Lys Met Thr Ala Gly Val Asn Arg Ile
    530                 535                 540

Ser Leu Leu Ser Ala Val Gly Leu Ala Asn Val Gly Trp His Phe
545                 550                 555                 560

Glu Arg Tyr Asn Gln Gly Val Leu Gly Pro Val Thr Leu Ser Gly Leu
                565                 570                 575

Asn Glu Gly Thr Arg Asp Leu Thr Trp Gln Tyr Trp Ser Tyr Lys Ile
                580                 585                 590

Gly Thr Lys Gly Glu Gln Gln Val Tyr Asn Ser Gly Gly Ser Ser
        595                 600                 605

His Val Gln Trp Gly Pro Pro Ala Trp Lys Gln Pro Leu Val Trp Tyr
    610                 615                 620

Lys Thr Thr Phe Asp Ala Pro Gly Gly Asn Asp Pro Leu Ala Leu Asp
625                 630                 635                 640

Leu Gly Ser Met Gly Lys Gly Gln Ala Trp Ile Asn Gly Gln Ser Ile
                645                 650                 655

Gly Arg His Trp Ser Asn Asn Ile Ala Lys Gly Ser Cys Asn Asp Asn
            660                 665                 670

Cys Asn Tyr Ala Gly Thr Tyr Thr Glu Thr Lys Cys Leu Ser Asp Cys
        675                 680                 685

Gly Lys Ser Ser Gln Lys Trp Tyr His Val Pro Arg Ser Trp Leu Gln
    690                 695                 700

Pro Arg Gly Asn Leu Leu Val Val Phe Glu Glu Trp Gly Gly Asp Thr
705                 710                 715                 720

Lys Trp Val Ser Leu Val Lys Arg Thr Ile Ala
                725                 730
```